(12) United States Patent
Kokaia

(10) Patent No.: US 11,072,804 B2
(45) Date of Patent: Jul. 27, 2021

(54) VECTOR

(71) Applicant: COMBIGENE AB, Lund (SE)

(72) Inventor: Merab Kokaia, Lund (SE)

(73) Assignee: Combigene AB, Lund (SE)

( * ) Notice: Subject to any disclaimer, the term of this patent is extended or adjusted under 35 U.S.C. 154(b) by 315 days.

(21) Appl. No.: 16/070,443

(22) PCT Filed: Feb. 10, 2017

(86) PCT No.: PCT/EP2017/053049
§ 371 (c)(1),
(2) Date: Jul. 16, 2018

(87) PCT Pub. No.: WO2017/137585
PCT Pub. Date: Aug. 17, 2017

(65) Prior Publication Data
US 2019/0024116 A1    Jan. 24, 2019

(30) Foreign Application Priority Data

Feb. 12, 2016  (SE) ..................... 1650192-6

(51) Int. Cl.
*C12N 15/86*     (2006.01)
*A61K 48/00*     (2006.01)
(Continued)

(52) U.S. Cl.
CPC .......... *C12N 15/86* (2013.01); *A61K 48/0058* (2013.01); *A61K 48/0075* (2013.01);
(Continued)

(58) Field of Classification Search
CPC .......... A61K 48/00; A61P 25/00; A61P 25/08; A61P 25/16; A61P 43/00; C07K 14/00;
(Continued)

(56) References Cited

U.S. PATENT DOCUMENTS

| 8,901,094 B2 * | 12/2014 | Kokaia ................ A61K 48/005 |
| | | 514/44 R |
| 2011/0288160 A1 * | 11/2011 | During ...................... A61P 3/10 |
| | | 514/44 R |

(Continued)

FOREIGN PATENT DOCUMENTS

| CN | 104313052 A | 1/2015 |
| EP | 2046394 | 12/2014 |

(Continued)

OTHER PUBLICATIONS

Richichi et al, J. Neurosci. 24(12): 3051-3059, 2004.*
(Continued)

*Primary Examiner* — Kevin K Hill
(74) *Attorney, Agent, or Firm* — Knobbe Martens Olson & Bear LLP

(57) ABSTRACT

The present invention relates to a recombinant adeno-associated viral (r AAV) vector comprising neuropeptide Y (NPY) coding sequence and neuropeptide Y2 receptor (NPY2R) coding sequence. The invention further relates to a AAV particle comprising said vector, wherein the vector is encapsulated by adeno-associated virus (AAV) capsid proteins. Also, a pharmaceutical composition comprising said AAV particle, for use in the prevention or treatment of a neurological disorder in mammals, such as epilepsy.

4 Claims, 8 Drawing Sheets

Specification includes a Sequence Listing.

(51) Int. Cl.
*C07K 14/575* (2006.01)
*C07K 14/72* (2006.01)

(52) U.S. Cl.
CPC ........ *C07K 14/57545* (2013.01); *C07K 14/72* (2013.01); *C12N 2750/14133* (2013.01); *C12N 2750/14143* (2013.01); *C12N 2800/22* (2013.01); *C12N 2830/001* (2013.01); *C12N 2840/203* (2013.01)

(58) Field of Classification Search
CPC .............. C07K 14/575; C07K 14/5745; C07K 14/705; C07K 14/72; C12N 15/79; C12N 15/86; C12N 15/864; C12N 15/8645; C12N 2750/14111; C12N 2750/14132; C12N 2750/14141; C12N 2750/14142; C12N 2750/14143; C12N 2800/22; C12N 2830/001; C12N 2830/20; C12N 2830/48; C12N 2840/00; C12N 2840/20; C12N 2840/203
See application file for complete search history.

(56) References Cited

U.S. PATENT DOCUMENTS

| | | | |
|---|---|---|---|
| 2012/0021039 A1* | 1/2012 | Kusk | A61K 9/0019 424/424 |
| 2014/0196176 A1* | 7/2014 | Heintz | C12N 15/1041 800/287 |

FOREIGN PATENT DOCUMENTS

| | | |
|---|---|---|
| WO | WO 2008/004972 | 1/2008 |
| WO | WO 2008/004972 A2 | 1/2008 |
| WO | WO 2009/120978 A2 | 10/2009 |
| WO | WO 2010/071454 A1 | 6/2010 |
| WO | WO 2015/089419 | 6/2015 |
| WO | WO 2015/139093 | 9/2015 |

OTHER PUBLICATIONS

Kapturczak et al, Molecular Therapy 5(2): 154-160, 2002.*
Carter et al, Human Gene Therapy 16: 541-550, 2005.*
Hollis et al, Molecular Therapy 16(2): 296-301, 2008.*
Perrin, Nature (507): 423-425, 2014.*
De Felipe et al, Current Gene Therapy 2: 355-378, 2002.*
Choi et al, Molecular Brain 7(17): doi.org/10.1186/1756-6606-7-17, 10 pages, Mar. 11, 2014.*
Burger et al, Molecular Therapy 19(2): 302-317, 2004.*
Bosch, Marie K. et al., "Dual Transgene Expression in Murine Cerebellar Purkinje Neurons by Viral Transduction In Vivo" PLOS ONE, Aug. 2014, pp. 1-17, vol. 9, Issue 8, e104062.
Chen, Yiwei "Range: Gene Transfer of Reversibly Controlled Polycistronic Genes" Molecular Therapy—Nucleic Acids, 2013, pp. 1-10, vol. 2, e85.
Woldbye, David P.D. et al., "Adeno-associated viral vector-induced overexpression of neuropeptide Y Y2 receptors in the hippocampus suppresses seizures" Brain, 2010, pp. 2778-2788, vol. 133.
International Search Report dated Apr. 18, 2017 for PCT/EP2017/053049, filed Feb. 10, 2017.

* cited by examiner

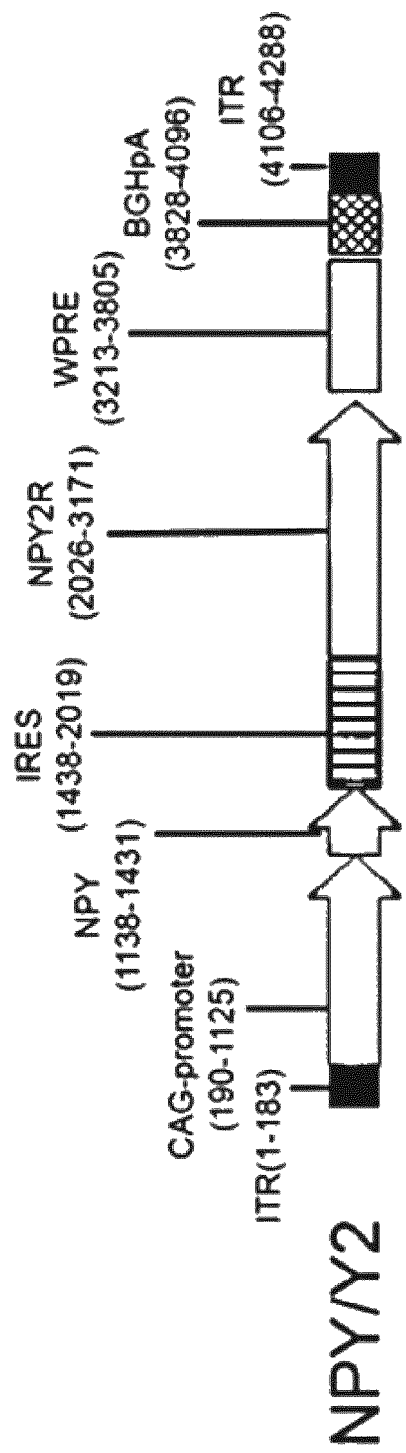
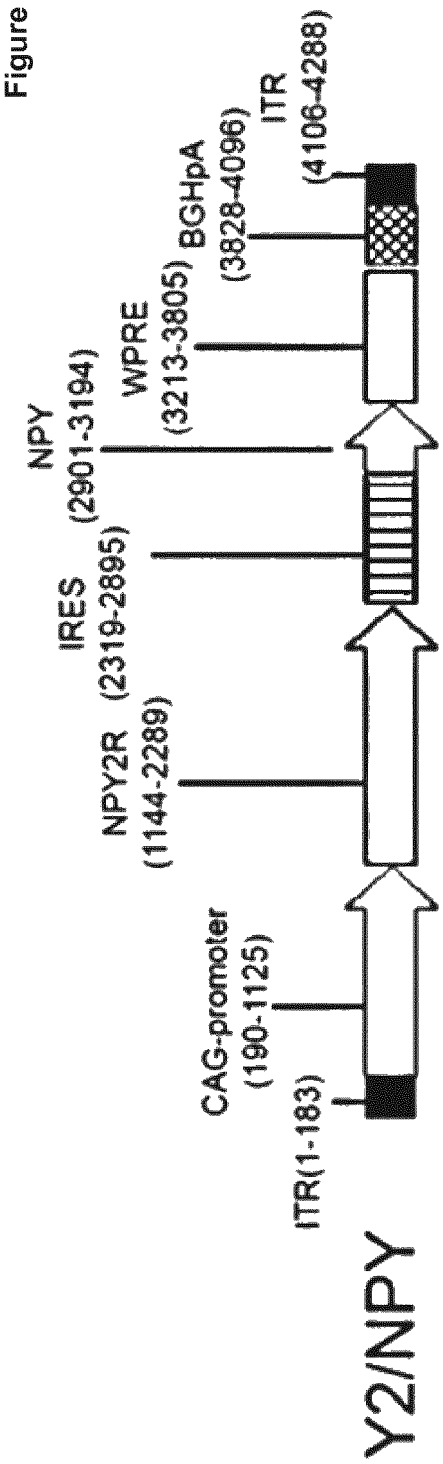
Figure 1A
Figure 1B

VECTOR

CROSS REFERENCE TO RELATED APPLICATIONS

This application is a U.S. National Phase Application of PCT International Application No. PCT/EP2017/053049, filed on Feb. 10, 2017, designating the United States of America and published in the English language, which is an International Application of and claims the benefit of priority to Swedish Patent Application No. 1650192-6, filed on Feb. 12, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-STROM018-001APC.txt, the date of creation of the ASCII text file is Jul. 5, 2018, and the size of the ASCII text file is 23 KB.

FIELD OF THE INVENTION

The present invention relates to a vector comprising certain nucleic acid sequences encoding NPY and its receptor Y2 (NPY2R) together with specific vector elements. Furthermore, the invention relates to said vector being encapsulated in capsid proteins from adeno-associated virus serotype 1, 2, and 8 forming AAV particles. Finally, the invention relates to said vector, or said AAV particles, being used in the preparation of a medicament for treatment of a neurological disorder in a mammal, such as epilepsy.

BACKGROUND OF THE INVENTION

According to the World Health Organization (WHO) the disorders relating to the central nervous system constitute a large socioeconomic health problem, and the currently available therapeutic options are insufficient. These disorders include but are not limited to epilepsy and Parkinson's disease.

Epilepsy is one of the world's oldest recognized neurological conditions, with written records dating back to 4000 BC. Fear, misunderstanding, discrimination and social stigma have surrounded epilepsy for centuries. This stigma continues in many countries today and can impact on the quality of life for people with the disorder and their families. About 1% of people worldwide suffer from epilepsy, making it one of the most common neurological diseases globally.

Epileptic seizures are episodes that can vary from brief and nearly undetectable to long periods of vigorous shaking. In epilepsy, seizures tend to recur, and often have no identifiable underlying cause.

Seizure episodes are a result of excessive electrical discharges in a group of synchronized brain cells. Different parts of the brain can be the site of such discharges. The most common type of epilepsy, which affects 6 out of 10 subjects suffering from the disorder, is called idiopathic epilepsy and has no identifiable cause. Epilepsy with a known cause is called secondary epilepsy, or symptomatic epilepsy. The causes of secondary (or symptomatic) epilepsy includes: brain damage from prenatal or perinatal injuries, congenital abnormalities or genetic conditions with associated brain malformations, a severe head injury, a stroke that restricts the amount of oxygen to the brain, an infection of the brain such as meningitis, encephalitis, neurocysticercosis, certain genetic syndromes, or a brain tumor.

It has been estimated that up to 70% of epilepsy cases can be treated with daily medication. However, for people who respond poorly to the treatment, they may have to remain untreated or resort to epilepsy surgery or to non-pharmacological treatment such as deep brain stimulation (DBS), vagus nerve stimulation (VNS), or diets.

According to WHO, epilepsy accounts for 0.75%, of the global burden of disease, a time-based measure that combines years of life lost due to premature mortality and time lived in less than full health. In 2012, epilepsy was responsible for approximately 20.6 million disability-adjusted life years (DALYs) lost. Epilepsy has significant economic implications in terms of health-care needs, premature death and lost work productivity.

Thus, there is a need for new approaches and subsequent new methods for treating epilepsy. In EP 2046394 A1, a promising approach for the treatment of disorders of the nervous system is described, wherein one or several neuropeptides are overexpressed in the cells of the nervous system together with and one or more of their corresponding receptors. Increased release of a neurotransmitter often leads to compensatory downregulation of the receptors mediating the effects of the neurotransmitter, thus expression of corresponding receptors helps avoid limiting therapeutic effect over time. An improved approach using the concept of neuropeptide and receptor overexpression would be advantageous for a new treatment for epilepsy, in particular for treatment of pharmacoresistant epilepsy, the types of epilepsy where current pharmaceutical treatment approaches donot lead to desired therapeutic effect.

SUMMARY OF THE INVENTION

Accordingly, aspects of the present invention preferably seek to mitigate, alleviate or eliminate one or more of the above-identified deficiencies in the art and disadvantages singly or in any combination and solve at least the above mentioned problems by providing a recombinant adenoassociated viral (rAAV) vector comprising neuropeptide Y (NPY) coding sequence and neuropeptide Y2 receptor (NPY2R) coding sequence.

According to one aspect of the invention, the vector further comprises at least one, preferably all, of the functional elements of: AAV2 Inverted Terminal Repeat sequences (ITR), hybrid cytomegalovirus enhancer/chicken beta-actin CAG promoter (CAG), internal ribosome entry site (IRES), woodchuck hepatitis post-translational regulatory element (WPRE), and/or bovine growth hormone polyadenylation (bGH-polyA) signal sequence.

In one aspect of the invention, an AAV particle comprises said vector, wherein the vector is encapsulated by adenoassociated virus (AAV) capsid proteins.

According to yet another aspect of the invention, a pharmaceutical composition comprises said AAV particle, for use in the prevention, inhibition, or treatment of a neurological disorder in a mammal, such as epilepsy or Parkinson's disease.

In one aspect of the invention, a method for treating, inhibiting, or ameliorating a neurological disorder in a subject, comprises administering into cells of the central nervous system of a subject, such as a mammalian or a human subject, suffering from a neurological disorder, such as Epilepsy or Parkinson's disease, a pharmaceutically effective amount of said composition.

According to another aspect of the invention, a method of delivery of an NPY and Y2 genome to a mammalian cell, comprises introducing into a cell said AAV particle. In yet another embodiment, a method of administering an NPY and Y2 genome to a subject, such as a mammalian or a human subject, comprises administering said cell to the subject.

In one aspect of the invention, a method of delivery of an NPY and Y2 genome to a subject, comprises administering to a mammalian cell in a subject said AAV particle, wherein the virus particle is administered to the hippocampus of the subject.

According to another aspect of the invention, a method of reducing a disease where NPY has a therapeutic effect or is caused by NPY-deficiency, wherein the disease is selected from Epilepsy or Parkinson's disease, comprises administering into cells of the central nervous system of a subject suffering from a neurological disorder, a pharmaceutically effective amount of said composition.

According to yet another aspect of the invention, a method of providing NPY to a subject in need thereof, such as a subject selected as one having an NPY deficiency by clinical evaluation or diagnostic test, such as e.g., EEG and/or clinical diagnosis of epilepsy or Parkinson's disease, comprises selecting a subject in need of NPY, such as a subject with an NPY deficiency, and providing said subject a pharmaceutically effective amount of said composition.

Other aspects of the invention also concern alternatives found in the claims of the application.

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIGS. 1 A and B are schematic presentations of the vectors used in several of the embodiments described herein, wherein the transgenic order of neuropeptide Y (NPY) and neuropeptide receptor 2 (NPY2R) is NPY being upstream of NPY2R (FIG. 1A) or NPY2R being upstream of NPY (FIG. 1B).

FIG. 7 shows a graphic illustrating the seizure development during a 2 hours period observation after a single kainate injection (s.c.) in relationship to the levels of AAV-induced transgene overexpression.

DESCRIPTION OF EMBODIMENTS

Figure 2:
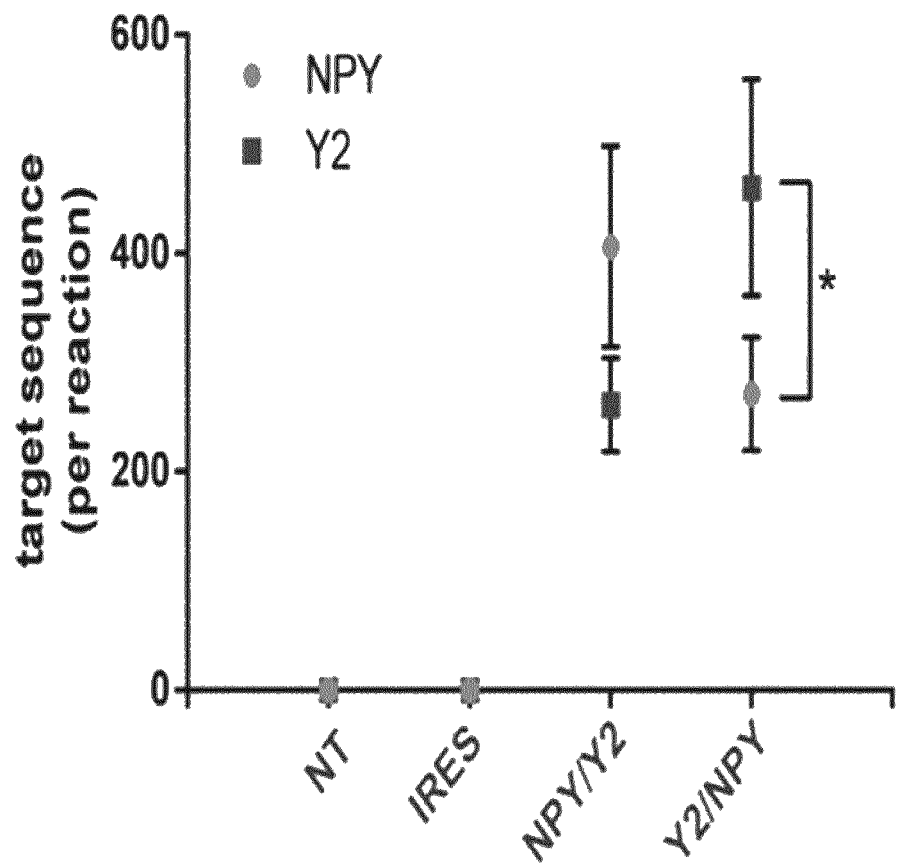
FIG. 2 shows a graph summarizing the transgene expression in transfected HEK293 cells by ddPCR. Number of NPY and NPY2R target sequences measured by ddPCR. As controls are used non-treated cells or an AAV expression plasmid without the NPY and NPY2R encoding sequences (IRES). Paired student's t-test, $t_3$=3.927, *P=0.0294. Data points/bars represent the mean+SEM (n=4 per treatment).

The following description focuses on an embodiment of the present invention applicable to AAV vectors for gene therapy and in particular to AAV particles of said vectors for the treatment of a neurological disorder in a mammal, such as epilepsy.

Neurological disorders include a large group of disorders in the nervous system including but not limited to the brain, spinal cord and other nerves, with structural, biochemical, and/or signalling abnormalities among others. Neurological disorders are not limited to humans, but are also found in other mammals such as horses, dogs and cats, referred to herein as "subjects". For example, incidences of Canine epilepsy in the general dog population are estimated to be between 0.5% and 5.7%.

Neuropeptide Y (NPY) is a 36 amino acid long peptide neurotransmitter and one of the most abundantly expressed in the mammalian central nervous system. NPY has been shown to exert neuroprotection in animal models of neurodegenerative diseases such as Alzheimer's (Rose et al., 2009), Huntington's, and Parkinson's disease. NPY was first shown to reduce excitation in Schaffer collateral CA1 synapses in rat hippocampal slices and subsequently shown to involve Y2 receptor-dependent inhibition of presynaptic glutamate release. Glutamate is the principal excitatory neurotransmitter in the brain and, as such responsible for initiation, spread, and out-of-scale synaptic transmission seen under seizure activity. Consistently, mutant mice deficient in NPY are more seizure-susceptible, and intracerebroventricular administration of NPY exerts anti-epileptiform effects in vivo in experimental seizure models in rats. Importantly, NPY also inhibits excitatory synaptic transmission in human epileptic hippocampus (Patrylo et al., 1999; Ledri et al., 2015). In the hippocampus antiepileptic effects of NPY are mediated predominantly via binding to Y2 or Y5 receptors (Woldbye et al., 1997, 2005; El Bahh et al., 2005; Benmaamar et al., 2005), whereas activation of Y1 receptors is seizure-promoting (Benmaamar et al., 2003).

Due to its anti-epileptic effects, NPY has been applied in targeted gene therapy. Thus rAAV-mediated hippocampal overexpression of NPY exerts a suppressant effects on stimulation-induced acute seizures in rats and on spontaneous seizures three months after status epilepticus insult. To capitalize on the differential NPY receptor subtype specific involvement, gene therapy has also been performed with overexpression of Y1, Y2, or Y5 receptors alone or combination with NPY. Thus combined hippocampal overexpression of NPY and Y2 or Y5 had a superior seizure-suppressant effect on stimulation-induced acute seizures in rats as compared to NPY or receptor overexpression alone (Woldbye et al., 2010; Gøtzsche et al., 2012).

In contrast, hippocampal overexpression of Y1 receptors lead to seizure-promoting effects as predicted by subsequent studies (Benmaamar et al., 2003; Olesen et al., 2012). In a similar approach rAAV vector mediated overexpression of the Y2 preferring agonist NPY13-36 also exerted anti-epileptic effects (Foti et al., 2007). Subsequently, the translational value of the anti-epileptic effects of NPY and Y2 receptor rAAV vector-mediated overexpression has gained further support, when tested in a clinically relevant long-term chronic model of epilepsy in rats (Ledri et al., 2016).

Described herein are several approaches for gene therapy utilizing AAV vectors s to treat or inhibit epilepsy and/or Parkinson's disease in a subject in need thereof. Moreover, AAV vectors are by now considered safe to use for delivery of therapeutic transgenes in treatment of neurological diseases (McCown, 2011; Bartus et al., 2014). However, the development of recombinant viral vectors efficient at expressing their therapeutic transgenes in a safe way has met several obstacles, which is an existing obstacle for their widespread use in human gene therapy. Thus, the design of new gene therapy involving rAAV vectors involves the careful selection of many different elements creating highly customized and unique constructs for the specific tissue and gene therapy target.

It was envisaged that a novel gene therapy comprising the overexpression of NPY and Y2 receptors encoded for by a single rAAV will generate efficient in vivo expression in view of the specific choices in vector arrangement and functional elements set forth herein (e.g., the ordering of genetic elements in the construct and/or the distances between certain genetic elements) when used in concert with particular AAV serotype capsid proteins. The disclosure presented below, provides greater detail on these compositions and methods of making and using these compositions to treat and/or inhibit epilepsy and/or Parkinson's disease in subjects that are in need of an agent that treats or ameliorates epilepsy or Parkinson's disease or maladies associated therewith, such as seizure activity.

rAAV NPY and NPY2R Vector

By having the NPY and NPY2R coding sequence in the same vector, NPY2R and NPY will be spread in a homologous manner, ensuring close proximity of expression of the effector molecule NPY and its target the seizure-inhibiting receptor NPY2R. Further, by having NPY and NPY2R coding sequence in the same vector, the number of genome insertions of NPY and NPY2R in one cell can be homologous, enabling a controlled ratio of inserted NPY and NPY2R genes.

Thus in a first embodiment, a recombinant adeno-associated viral (rAAV) vector comprises a neuropeptide Y (NPY; c.f. SEQ ID NO:15) coding sequence and a neuropeptide Y2 receptor (NPY2R; c.f SEQ ID NO:16) coding sequence.

The Neuropeptide Y (NPY) coding sequence in the vector may have a sequence corresponding to SEQ ID NO: 1 or share at least 90% sequence identity, such as at least 95%, 96%, 97%, 98% or 99% sequence identity (% SI) to SEQ ID NO: 1. The neuropeptide Y (NPY) coding sequence may be truncated as long as it encodes a functional neuropeptide Y e.g., the molecule can bind its receptor. A truncated sequence may comprise at least 255, such as 265, 275, 285, 290 (out of 294) bases and share at least 90% sequence identity, such as at least 95%, 96%, 97%, 98% or 99% sequence identity (% SI) to SEQ ID NO: 1 and encode a functional neuropeptide Y, e.g., the molecule can bind its receptor.

The neuropeptide Y2 receptor (NPY2R) coding sequence in the vector may have a sequence corresponding to SEQ ID NO: 2 or share at least 90% sequence identity, such as at least 95%, 96%, 97%, 98% or 99% sequence identity (% SI) to SEQ ID NO: 2. The neuropeptide Y2 receptor (NPY2R) coding sequence may be truncated as long as it is a functional neuropeptide Y2 receptor, e.g., the molecule can bind its ligand. A truncated sequence may comprise at least 975, such as 1000, 1115, 1130, 1140 (out of 1146) bases and share at least 90% sequence identity, such as at least 95%, 96%, 97%, 98% or 99% sequence identity (% SI) to SEQ ID NO: 2 and encode a functional neuropeptide Y2 receptor, e.g., the molecule can bind its ligand.

Although receptor abundance is a factor in tissue-specific expression, other elements of the AAV vector can affect tissue-specific expression. Further expression control is given in the vector design by control of the transgene orientation, that is, the order of the NPY and NPY2R genes and/or the distances with respect to promoter elements and/or enhancer elements from the genes encoding NPY and/or NPY2R in the vector, as described below. The transcriptional interference caused by endogenous gene promoters or from the promoter elements or enhancer elements affect the transgene expression at the locus. Thus, the vector has been modified to improve transgene expression with respect to the selected vector promoter elements and/or enhancer elements, as compared to conventional vector designs, which lack these modifications. In a first embodiment, the transgene orientation of NPY and NPY2R encoding genes in the vector is such that the NPY encoding gene precedes the NPY2R encoding gene in terms of proximity to the promoter (e.g., the NPY encoding gene is presented on the vector upstream of the NPY2R encoding gene such that it is more proximal to the promoter than the NPY2R encoding gene). Said neuropeptide Y (NPY) encoding sequence may have a sequence corresponding to SEQ ID NO:1 or a sequence having at least 90% sequence identity, such as at least 95%, 96%, 97%, 98% or 99% sequence identity (% SI) to said sequence. Said neuropeptide Y2 receptor (NPY2R) encoding sequence may have a sequence corresponding to SEQ ID NO:2 or a sequence having at least 90%, such as at least 95%, 96%, 97%, 98% or 99% sequence identity (% SI) to said sequence. Through gene expression, the neuropeptide Y (NPY) coding sequence is used in the synthesis of pro-neuropeptide Y preproprotein (SEQ ID NO: 15) and the neuropeptide Y2 receptor (NPY2R) coding sequence is used in the synthesis of neuropeptide Y receptor type 2 (SEQ ID NO: 16). As known to the skilled person, it is possible that alternative sequences may also encode for the same peptide sequence. Thus, the recombinant adeno-associated viral (rAAV) vector may also comprise a sequence encoding a protein according to SEQ ID NO: 15, or a sequence having at least 90% sequence identity, such as at least 95%, 96%, 97%, 98% or 99% sequence identity (% SI) to said sequence and a sequence coding for a protein according to SEQ ID NO:16, or a sequence having at least 90% sequence identity, such as at least 95%, 96%, 97%, 98% or 99% sequence identity (% SI) to said sequence. The NPY encoding gene may be juxtaposed to said promoter. The NPY encoding gene may start within 5-60, 5-50, 5-40, 5-30, 5-20, 5-15, or 5-10 nucleotides from the end of the promoter region (e.g., the NPY encoding gene starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides from the end of the promoter region or the NPY encoding gene starts within a range defined by any two of the aforementioned number of nucleotide positions from the promoter). The promoter may be the cytomegalovirus enhancer/chicken β-actin (CAG) promoter. The CAG promoter sequence in the vector may share at least 90% sequence identity, such as at least 95%, 96%, 97%, 98% or 99% sequence identity (% SI) to SEQ ID NO: 4. The CAG promoter sequence may be truncated as long as it is functional (e.g., induces expression of a gene), and a truncated CAG promoter sequence may comprise at least 850, such as 875, 900, 925, 935 (out of 936) bases and share at least 90% sequence identity, such as at least 95%, 96%, 97%, 98% or 99% sequence identity (% SI) to SEQ ID NO: 4 and induce the expression of a gene that is operationally linked to said promoter. The CAG promoter may have a sequence corresponding to SEQ ID NO:4 or a sequence having at least 90% sequence identity, such as at least 95%, 96%, 97%, 98% or 99% sequence identity (% SI) to SEQ ID NO: 4. An IRES sequence may be positioned between the NPY and NPY2R encoding genes in the vector. The IRES sequence may start within 5-50, 5-40, 5-30, 5-20, 5-15, or 5-10 nucleotides from the end of the NPY encoding gene (e.g., the IRES sequence starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the end of the NPY encoding gene or the IRES sequence starts within a range defined by any two of the aforementioned number of nucleotide positions from the NPY encoding sequence). The IRES sequence may end within 5-50, 5-40, 5-30, 5-20, 5-15, or 5-10 nucleotides from the start of the NPY2R encoding gene (e.g., the IRES sequence ends 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the start of the NPY2R encoding gene or the IRES sequence ends within a range defined by any two of the aforementioned number of nucleotide positions from the start of the NPY2R encoding sequence). The IRES sequence may be a A7 EMCV IRES sequence. The A7 EMCV IRES sequence in the vector may share at least 90% sequence identity, such as at least 95%, 96%, 97%, 98% or 99% sequence identity (% SI) to SEQ ID NO: 3. The A7 EMCV IRES sequence may be truncated as long as it is functional (e.g., induce gene expression), and a truncated A7 EMCV IRES sequence may comprise at least 525, 545, 560, 570, or 575 (out of 582) bases and share at least 90% sequence identity, such as at least 95%, 96%, 97%, 98% or 99% sequence identity (% SI) to SEQ ID NO: 3. The IRES may have a sequence corresponding to SEQ ID NO:3 or a sequence having at least 90% sequence identity, such as at least 95%, 96%, 97%, 98% or 99% sequence identity (% SI) to SEQ ID NO: 3. A woodchuck hepatitis post transcriptional regulatory element (WPRE) may be positioned downstream of the NPY and NPY2R encoding genes in the vector and, optionally the WPRE is proximal to and/or juxtaposed to the NPY2R encoding gene. A WPRE sequence may be positioned downstream from the NPY2R encoding gene in the vector. The WPRE sequence may start within 5-80, 5-70, 5-60, 5-50, 5-40, 5-30, 5-20, 5-15, or 5-10 nucleotides from the end of the NPY2R encoding gene (e.g., the WPRE sequence starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides from the end of the NPY2R encoding gene or the WPRE sequence starts within a range defined by any two of the aforementioned number of nucleotide positions from the NPY2R encoding sequence). The WPRE sequence in the vector may share at least 90% sequence identity, such as at least 95%, 96%, 97%, 98% or 99% sequence identity (% SI) to SEQ ID NO: 5. This sequence has 100% homology with base pairs 1093 to 1684 of the Woodchuck hepatitis B virus (WHV8) genome. The WPRE sequence may be truncated as long as it is functional, and a truncated WPRE sequence may comprise at least 525, 545, 555, 565, 575, or 585 (out of 593) bases and share at least 90%, such as at least 95%, 96%, 97%, 98% or 99% sequence identity (% SI) to SEQ ID NO: 5. The WRPE may have a sequence corresponding to SEQ ID NO:5 or a sequence having at least 90% sequence identity, such as at least 95%, 96%, 97%, 98% or 99% sequence identity (% SI) to SEQ ID NO: 5. The vector may comprise a bovine growth hormone polyadenylation signal (BGHpA), which is positioned downstream from NPY and NPY2R encoding genes in the vector and, optionally is proximal to and/or juxtaposed to the WPRE. A BGHpA sequence may be positioned downstream from the WPRE sequence. The BGHpA sequence may start within 5-50, 5-40, 5-30, 5-20, 5-15, or 5-10 nucleotides from the end of the WPRE sequence (e.g., the BGHpA sequence starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the end of the WPRE sequence or the BGHpA sequence starts within a range defined by any two of the aforementioned number of nucleotide positions from the WPRE sequence). The BGHpA sequence, also referred to as a "BGHpA signal sequence" in the vector may share at least 90% sequence identity, such as at least 95%, 96%, 97%, 98% or 99% sequence identity (% SI) to SEQ ID NO: 6. The BGHpA signal sequence may be truncated as long as it is functional, and a truncated BGHpA signal sequence may comprise at least 225, 235, 245, 255, or 265 (out of 269) bases and share at least 90% sequence identity, such as at least 95%, 96%, 97%, 98% or 99% sequence identity (% SI) to SEQ ID NO: 6. The BGHpA signal may have a sequence corresponding to SEQ ID NO:6 or sequence a sequence having at least 90% sequence identity, such as at least 95%, 96%, 97%, 98% or 99% sequence identity (% SI) to SEQ ID NO: 6. The vector may also comprise a first AAV2 inverted terminal repeat (ITR) domain positioned upstream from the promoter and/or a second ITR domain positioned downstream from the NPY and NPY2R encoding genes in the vector, preferably the second ITR domain is positioned proximal to the BGHpA domain. The 5'-end ITR sequence in the vector may share at least 90% sequence identity, such as at least 95%, 96%, 97%, 98% or 99% sequence identity (% SI) to SEQ ID NO: 7. The 5'-end ITR sequence may be truncated as long as it is functional, and a truncated ITR sequence may comprise at least 145, such as 155, 165, 175, 180 (out of 183) bases and share at least 90% sequence identity, such as at least 95%, 96%, 97%, 98% or 99% sequence identity (% SI) to SEQ ID NO: 7. The 3'-end ITR sequence in the vector may share at least 90% sequence identity, such as at least 95%, 96%, 97%, 98% or 99% sequence identity (% SI) to SEQ ID NO: 8. The 3'-end ITR sequence may be truncated as long as it is functional, and a truncated ITR sequence may comprise at least 145, such as 155, 165, 175, 180 (out of 183) bases and share at least 90%, such as at least 95%, 96%, 97%, 98% or 99% sequence identity (% SI) to SEQ ID NO: 8. The 5' end ITR may have a sequence corresponding to SEQ ID NO:7 or a sequence having at least 90% sequence identity, such as at least 95%, 96%, 97%, 98% or 99% sequence identity (% SI) to SEQ ID NO:7 and the 3' end ITR have a sequence corresponding to SEQ ID NO:8 or a sequence having at least 90% sequence identity, such as at least 95%, 96%, 97%, 98% or 99% sequence identity (% SI) to SEQ ID NO:8. Any one or more of the aforementioned genes may be codon optimized for expression in humans. As described below, three AAV serotypes were found to be effective for gene delivery of the vectors described herein: AAV2, AAV1 and AAV8. Accordingly, the vectors described above may be packaged with AAV capsid proteins that are selected from the group consisting of AAV1, AAV2 and AAV8. Also, as described below, it was found that vectors packaged with AAV1 capsid proteins performed better in tests in an epileptic seizure model, thus, preferred packaging of the vectors is with AAV1 capsid proteins.

In a second embodiment, the transgene orientation of NPY and NPY2R encoding genes in the vector is such that the NPY2R encoding gene precedes the NPY encoding gene such that it is more proximal to the promoter (e.g., the NPY2R encoding gene is presented on the vector upstream of the NPY encoding gene such that it is more proximal to the promoter than the NPY encoding gene). Said neuropeptide Y (NPY) encoding sequence may have a sequence corresponding to SEQ ID NO:1 or a sequence having at least 90% sequence identity, such as at least 95%, 96%, 97%, 98% or 99% sequence identity (% SI) to said sequence. Said neuropeptide Y2 receptor (NPY2R) encoding sequence may have a sequence corresponding to SEQ ID NO:2 or a sequence having at least 90%, such as at least 95%, 96%, 97%, 98% or 99% sequence identity (% SI) to said sequence. Through gene expression, the neuropeptide Y (NPY) coding sequence is used in the synthesis of pro-neuropeptide Y preproprotein (SEQ ID NO: 15) and the neuropeptide Y2 receptor (NPY2R) coding sequence is used in the synthesis of neuropeptide Y receptor type 2 (SEQ ID NO: 16). As known to the skilled person, it is possible that alternative sequences may also encode for the same peptide sequence. Thus, the recombinant adeno-associated viral (rAAV) vector may comprise a sequence encoding a protein according to SEQ ID NO: 15, or a sequence having at least 90% sequence identity, such as at least 95%, 96%, 97%, 98% or 99% sequence identity (% SI) to said sequence and a sequence coding for a protein according to SEQ ID NO:16, or a sequence having at least 90% sequence identity, such as at least 95%, 96%, 97%, 98% or 99% sequence identity (% SI) to said sequence. The NPY encoding gene may be juxtaposed to said promoter. The NPY2R encoding gene may start within 5-60, 5-50, 5-40, 5-30, 5-20, 5-15, or 5-10 nucleotides from the end of the promoter region (e.g., the NPY2R encoding gene starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides from the end of the promoter region or the NPY2R encoding gene starts within a range defined by any two of the aforementioned number of nucleotide positions from the promoter). The promoter may be the cytomegalovirus enhancer/chicken β-actin (CAG) promoter. The CAG promoter sequence in the vector may share at least 90% sequence identity, such as at least 95%, 96%, 97%, 98% or 99% sequence identity (% SI) to SEQ ID NO: 4. The CAG promoter sequence may be truncated as long as it is functional (e.g., induces expression of a gene), and a truncated CAG promoter sequence may comprise at least 850, such as 875, 900, 925, 935 (out of 936) bases and share at least 90% sequence identity, such as at least 95%, 96%, 97%, 98% or 99% sequence identity (% SI) to SEQ ID NO: 4 and induce the expression of a gene that is operationally linked to said promoter. The CAG promoter may have a sequence corresponding to SEQ ID NO:4 or a sequence having at least 90% sequence identity, such as at least 95%, 96%, 97%, 98% or 99% sequence identity (% SI) to SEQ ID NO: 4. An IRES sequence may be positioned between the NPY and NPY2R encoding genes in the vector. The IRES sequence may start within 5-50, 5-40, 5-30, 5-20, 5-15, or 5-10 nucleotides from the end of the NPY2R encoding gene (e.g., the IRES sequence starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the end of the NPY2R encoding gene or the IRES sequence starts within a range defined by any two of the aforementioned number of nucleotide positions from the NPY2R encoding sequence). The IRES sequence may end within 5-50, 5-40, 5-30, 5-20, 5-15, or 5-10 nucleotides from the start of the NPY encoding gene (e.g., the IRES sequence ends 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the start of the NPY encoding gene or the IRES sequence ends within a range defined by any two of the aforementioned number of nucleotide positions from the start of the NPY encoding sequence). The IRES sequence may be a A7 EMCV IRES sequence. The A7 EMCV IRES sequence in the vector may share at least 90% sequence identity, such as at least 95%, 96%, 97%, 98% or 99% sequence identity (% SI) to SEQ ID NO: 3. The A7 EMCV IRES sequence may be truncated as long as it is functional (e.g., induce gene expression), and a truncated A7 EMCV IRES sequence may comprise at least 525, 545, 560, 570, or 575 (out of 582) bases and share at least 90% sequence identity, such as at least 95%, 96%, 97%, 98% or 99% sequence identity (% SI) to SEQ ID NO: 3. The IRES may have a sequence corresponding to SEQ ID NO:3 or a sequence having at least 90% sequence identity, such as at least 95%, 96%, 97%, 98% or 99% sequence identity (% SI) to SEQ ID NO: 3. A woodchuck hepatitis post transcriptional regulatory element (WPRE) may be positioned downstream of the NPY and NPY2R encoding genes in the vector and, optionally the WPRE is proximal to and/or juxtaposed to the NPY encoding gene. A WPRE sequence may be positioned downstream from the NPY encoding gene in the vector. The WPRE sequence may start within 5-80, 5-70, 5-60, 5-50, 5-40, 5-30, 5-20, 5-15, or 5-10 nucleotides from the end of the NPY encoding gene (e.g., the WPRE sequence starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides from the end of the NPY encoding gene or the WPRE sequence starts within a range defined by any two of the aforementioned number of nucleotide positions from the NPY encoding sequence). The WPRE sequence in the vector may share at least 90% sequence identity, such as at least 95%, 96%, 97%, 98% or 99% sequence identity (% SI) to SEQ ID NO: 5. This sequence has 100% homology with base pairs 1093 to 1684 of the Woodchuck hepatitis B virus (WHV8) genome. The WPRE sequence may be truncated as long as it is functional, and a truncated WPRE sequence may comprise at least 525, 545, 555, 565, 575, or 585 (out of 593) bases and share at least 90%, such as at least 95%, 96%, 97%, 98% or 99% sequence identity (% SI) to SEQ ID NO: 5. The WRPE may have a sequence corresponding to SEQ ID NO:5 or a sequence having at least 90% sequence identity, such as at least 95%, 96%, 97%, 98% or 99% sequence identity (% SI) to SEQ ID NO: 5. The vector may comprise a bovine growth hormone polyadenylation signal (BGHpA), which is positioned downstream from NPY and NPY2R encoding genes in the vector and, optionally is proximal to and/or juxtaposed to the WPRE. A BGHpA sequence may be positioned downstream from the WPRE sequence. The BGHpA sequence may start within 5-50, 5-40, 5-30, 5-20, 5-15, or 5-10 nucleotides from the end of the WPRE sequence (e.g., the BGHpA sequence starts 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the end of the WPRE sequence or the BGHpA sequence starts within a range defined by any of the aforementioned number of nucleotide positions from the WPRE sequence). The BGHpA sequence, also referred to as a "BGHpA signal sequence" in the vector may share at least 90% sequence identity, such as at least 95%, 96%, 97%, 98% or 99% sequence identity (% SI) to SEQ ID NO: 6. The BGHpA signal sequence may be truncated as long as it is functional, and a truncated BGHpA signal sequence may comprise at least 225, 235, 245, 255, or 265 (out of 269) bases and share at least 90% sequence identity, such as at least 95%, 96%, 97%, 98% or 99% sequence identity (% SI) to SEQ ID NO: 6. The BGHpA signal may have a sequence corresponding to SEQ ID NO:6 or a sequence having at least 90% sequence identity, such as at least 95%, 96%, 97%, 98% or 99% sequence identity (% SI) to SEQ ID NO: 6. The vector may also comprise a first AAV2 inverted terminal repeat (ITR) domain positioned upstream from the promoter and/or a second ITR domain positioned downstream from the NPY and NPY2R encoding genes in the vector, preferably the second ITR domain is positioned proximal to the BGHpA domain. The 5'-end ITR sequence in the vector may share at least 90% sequence identity, such as at least 95%, 96%, 97%, 98% or 99% sequence identity (% SI) to SEQ ID NO: 7. The 5'-end ITR sequence may be truncated as long as it is functional, and a truncated ITR sequence may comprise at least 145, such as 155, 165, 175, 180 (out of 183) bases and share at least 90% sequence identity, such as at least 95%, 96%, 97%, 98% or 99% sequence identity (% SI) to SEQ ID NO: 7. The 3'-end ITR sequence in the vector may share at least 90% sequence identity, such as at least 95%, 96%, 97%, 98% or 99% sequence identity (% SI) to SEQ ID NO: 8. The 3'-end ITR sequence may be truncated as long as it is functional, and a truncated ITR sequence may comprise at least 145, such as 155, 165, 175, 180 (out of 183) bases and share at least 90%, such as at least 95%, 96%, 97%, 98% or 99% sequence identity (% SI) to SEQ ID NO: 8. The 5' end ITR may have a sequence corresponding to SEQ ID NO:7 or a sequence having at least 90% sequence identity, such as at least 95%, 96%, 97%, 98% or 99% sequence identity (% SI) to SEQ ID NO:7 and the 3' end ITR have a sequence corresponding to SEQ ID NO:8 or a sequence having at least 90% sequence identity, such as at least 95%, 96%, 97%, 98% or 99% sequence identity (% SI) to SEQ ID NO:8. Any one or more of the aforementioned genes may be codon optimized for expression in humans. As described below, three AAV serotypes were found to be effective for gene delivery of the vectors described herein: AAV2, AAV1 and AAV8. Accordingly, the vectors described above may be packaged with AAV capsid proteins that are selected from the group consisting of AAV1, AAV2 and AAV8. Also, as described below, it was found that vectors packaged with AAV1 capsid proteins performed better in tests in an epileptic seizure model, thus, preferred packaging of the vectors is with AAV1 capsid proteins. More disclosure on specific elements of these vectors and packaging systems are provided in the following passages.

Adeno-Associated Virus

Adeno-associated viruses (AAV) constitute a group of small non-enveloped DNA viruses from the Parvoviridae family known to infect humans, primates and non-primate animal species (such as cats and dogs and many others). AAV is not currently known to cause disease, and the virus causes a very mild immune response. Gene therapy vectors using AAV can transduce, i.e., enter and start up transgene expression, both dividing and quiescent cells (the state of a cell when it is not dividing) and persist without integrating into the genome of the host cell in an extrachromosomal state (some integration of virally carried genes into the host genome on a specific site at the human chromosome 19 does occur in the native virus). These features make AAV very attractive for creating viral vectors for gene therapy.

As of 2005, at least 110 non-redundant AAV serotypes were found and described in tissue samples from human and non-human primates. Serotypes are distinct variations within a species of bacteria or virus or among immune cells of different individuals, classified together based on their cell surface antigens, allowing the serologic and epidemiologic classification of organisms to the sub-species level. All of the known AAV serotypes can infect cells from multiple diverse tissue types. Tissue-specificity is determined by the capsid serotype of AAV vectors and this can be altered by pseudotyping, i.e. changing the serotype-specific capsid proteins to alter their tropism range which is important to their use in therapy. Out of these, serotype 2 (AAV2) has been the most extensively examined so far. AAV2 presents natural tropism towards skeletal muscles, neurons, vascular smooth muscle cells and hepatocytes. Three cell receptors have been described for AAV2: heparan sulfate proteoglycan (HSPG), aVβ5 integrin and fibroblast growth factor receptor 1 (FGFR-1), and it is thought that the first functions as a primary receptor.

Three AAV serotypes were found to be effective for gene delivery of the vectors described herein: AAV2, AAV1 and AAV8. In the brain, these AAV serotypes show neuronal tropism.

Comparative studies with a vector consisting of an AAV2-based genomic structure, pseudo-typing with capsid proteins from AAV serotype 1, 2, or 8, and interchangeable promoter (CMV, CaMKII or Syn I) in the cerebral cortex of marmoset, mouse and macaque, revealed serotype-specific distinct features in tropism, spread, and efficiencies of transduction and transgene expression (Watakabe et al., 2015).

Overall AAV2 was distinct from other serotypes with smaller spreading of the vector and a natural occurring neuronal tropism. However, all serotypes were able to induce transgene expression in neurons under neuron-specific promoters (CaMKII or Syn1), and with the exception of serotype 2 viral spread did not differ among other serotypes. All of the proposed serotypes appear to be suitable for AAV vector-mediated delivery of transgene into the brain.

Serotype 1 and 8 appear comparable and more efficient than serotype 2 in spread and transgene expression. Serotypes 1, 2, and 8 have all been proven capable of transducing glia and neurons and cell subtype specific restriction seems better achieved by distinct promoter choice.

In one embodiment, the AAV capsid proteins are selected from the group consisting of AAV1, AAV2 and AAV8.

AAV Vector Genomic Elements

In order to produce AAV vectors suitable for inducing expression of the transgenes, the elements in the AAV expression cassettes have been carefully evaluated and selected. This includes ITR sequences, promoter, multicistronic expression elements for the expression of multiple transgene from one vector, and enhancer elements.

ITR Sequences

The inverted terminal repeat (ITR) sequences are the only preserved genetic elements from the wildtype genome used and these sequences are necessary for several cis-acting processes, including self-priming for second DNA strand synthesis and encapsidation of DNA in the AAV particles. The Inverted Terminal Repeat (ITR) sequences were named after their symmetry, which appears to be required for efficient multiplication of the AAV genome. They gain this property by their ability to form a hairpin, which contributes to so-called self-priming that allows primase-independent synthesis of the second DNA strand. The ITRs have been shown to be required for both integration of the AAV DNA into the host cell genome (19th chromosome in humans), as well as, for efficient encapsidation of the AAV DNA combined with generation of a fully assembled, deoxyribonuclease-resistant AAV particles. Of the selection of available ITR-sequences, the AAV serotype 2 has been selected for many of the vectors described herein, which enabled efficient packing of the vectors into either AAV1, AAV2 or AAV8 capsids so as to generate virions, as described below. Being terminal repeats, the two ITR sequences are located at the 5'-end and the 3'-end of the vector respectively.

In one embodiment, two ITR sequences are located at the 5'-end and the 3'-end of the vector respectively, upstream and downstream of the coding sequences for NPY and NPY2R.

The 5'-end ITR sequence in the vector of the invention may share at least 90% sequence identity, such as at least 95%, 96%, 97%, 98% or 99% sequence identity (% SI) to SEQ ID NO: 7. The 5'-end ITR sequence may be truncated as long as it is functional, and a truncated ITR sequence may comprise at least 145, such as 155, 165, 175, 180 (out of 183) bases and share at least 90% sequence identity, such as at least 95%, 96%, 97%, 98% or 99% sequence identity (% SI) to SEQ ID NO: 7.

The 3'-end ITR sequence in the vector may share at least 90% sequence identity, such as at least 95%, 96%, 97%, 98% or 99% sequence identity (% SI) to SEQ ID NO: 8. The 3'-end ITR sequence may be truncated as long as it is functional, and a truncated ITR sequence may comprise at least 145, such as 155, 165, 175, 180 (out of 183) bases and share at least 90%, such as at least 95%, 96%, 97%, 98% or 99% sequence identity (% SI) to SEQ ID NO: 8.

In one embodiment, the 5' end ITR have a sequence corresponding to SEQ ID NO:7 or a sequence having at least 90% sequence identity, such as at least 95%, 96%, 97%, 98% or 99% sequence identity (% SI) to SEQ ID NO:7 and the 3' end ITR have a sequence corresponding to SEQ ID NO:8 or a sequence having at least 90% sequence identity, such as at least 95%, 96%, 97%, 98% or 99% sequence identity (% SI) to SEQ ID NO:8.

CAG Promoter

In genetics, a promoter is a region of DNA that initiates transcription of a particular gene. Promoters are located near the transcription start sites of genes, on the same strand and upstream on the DNA (towards the 5' region of the sense strand).

Normally, a promoter is between 100-1000 base pairs long. Generally, promoters have been classified in two major classes, namely TATA and CpG. However, genes using the same combinatorial formation of transcription factors have different gene expression patterns. Furthermore, in humans it has been found that different tissues use distinct classes of promoters.

The effects of various promoter sequences on transduction rates and gene expression levels will vary between cell types. A broad range of available promoters have been examined and evaluated to enable selection of the optimal one. In the current invention, CAG promoter has been found to provide suitable gene expression triggering in the target tissue. Several of the previously conducted clinical trials using AAV vectors for gene therapy have faced problems in obtaining high enough efficacy for therapeutic beneficial effects. Therefore the CAG promoter that is known as a strong synthetic promoter used to drive high levels of gene expression in mammalian expression vectors was chosen. It has been found that for many tissue types, the CAG promoter gives higher levels of expression than other commonly used cellular promoters such as the UBC and PGK promoters. The CAG promoter comprises the following sequences: (C) cytomegalovirus (CMV) early enhancer element, (A) promoter, first exon and the first intron of chicken beta-actin gene, (G) splice acceptor of the rabbit beta-globin gene. As such, it is not a promoter in a strict sense, as it includes a part of the transcribed sequence (two exons and an intron) and enhancer elements.

In one embodiment, the CAG promoter sequence is located upstream of the coding sequences for NPY and NPY2R.

The CAG promoter sequence in the vector of the invention may share at least 90% sequence identity, such as at least 95%, 96%, 97%, 98% or 99% sequence identity (% SI) to SEQ ID NO: 4.

The CAG promoter sequence may be truncated as long as it is functional (e.g., induces expression of a gene), and a truncated CAG promoter sequence may comprise at least 850, such as 875, 900, 925, 935 (out of 936) bases and share at least 90% sequence identity, such as at least 95%, 96%, 97%, 98% or 99% sequence identity (% SI) to SEQ ID NO: 4 and induce the expression of a gene that is operationally linked to said promoter.

In one embodiment, the CAG promoter has a sequence corresponding to SEQ ID NO:4 or a sequence having at least 90% sequence identity, such as at least 95%, 96%, 97%, 98% or 99% sequence identity (% SI) to SEQ ID NO: 4.

IRES

An internal ribosome entry site, abbreviated IRES, is a nucleotide sequence that allows for translation initiation in the middle of a messenger RNA (mRNA) sequence as part of the greater process of protein synthesis. Normally, translation can be initiated only at the 5' end of the mRNA molecule in eukaryotes, since 5' cap recognition is required for the assembly of the initiation complex. By incorporating an IRES sequences into the vector, bi-cistronic expression is allowed for the two genes from the single vector, here the first gene is initiated at the normal 5' cap, and the second at the IRES.

Furthermore, while the NPY and NPY2R rAAV vector allows for homogenous insertion of NPY and NPY2R in one cell, the incorporation of the IRES element allows for heterogeneous expression of NPY and NPY2R genes. Furthermore, by selecting the transgenic orientation of NPY and NPY2R genes, it is possible to alternate the expression ratio between the two transgene as described above. Thereby, a suitable balance of the ratio of NPY and NPY2R in vivo expression can be achieved for the target tissue and treatment.

In one embodiment, the IRES sequence is located between the coding sequences for NPY and NPY2R.

There are several different viral IRES sequences currently known, such as picornavirus IRES, different Hepatitis virus IRES and cripavirus IRES.

Out of the possible known IRES sequences, the inventor has found that the internal ribosomal entry site (IRES) from encephalomyocarditis virus (EMCV) harbouring a modified A7 sequence was the best suitable for the vector.

IRES from encephalomyocarditis virus are commonly used in experimental and pharmaceutical applications to express proteins in eukaryotic cells or cell-free extracts, and it confers a high level of cap-independent translation activity to appropriately configured cistrons. The modified A7 sequence (Rees et al., 1996; Bochkov and Palmenberg, 2006) has been shown to achieve better cistron translation for the A7 EMCV IRES than a non-modified EMCV IRES.

The A7 EMCV IRES sequence in the vector of the invention may share at least 90%, such as at least 95%, 96%, 97%, 98% or 99% sequence identity (% SI) to an oligonucleotide sequence of the corresponding length present in SEQ ID NO: 3.

The A7 EMCV IRES sequence may be truncated as long as it is functional, and a truncated A7 EMCV IRES sequence may comprise at least 525, 545, 560, 570, or 575 (out of 582) bases and share at least 90%, such as at least 95%, 96%, 97%, 98% or 99% sequence identity (% SI) to a oligonucleotide sequence of the corresponding length present in SEQ ID NO: 3.

In one embodiment, the IRES have a sequence corresponding to SEQ ID NO:3 or a sequence having at least 90%, such as at least 95%, 96%, 97%, 98% or 99% sequence identity (% SI) to a oligonucleotide fragment of the corresponding length present in SEQ ID NO: 3.

WPRE

To ensure gene expression in target cells, the delivery and level of transcription can be optimized. However, one can also apply post-transcriptional methods for improving gene expression. The vector of the invention may incorporate a woodchuck hepatitis post-transcriptional regulatory element (WPRE). WPRE is a DNA sequence which helps increasing transgene expression by formation of a specific tertiary structure, thereby enhancing the expression of heterologous genes post-transcriptionally. WPRE is a tripartite regulatory element with gamma, alpha, and beta components. In the vector of the invention, the full tripartite WPRE have been incorporated, for full WPRE activity.

In one embodiment, the WPRE sequence is located downstream from the coding sequences for NPY and NPY2R.

The WPRE sequence in the vector of the invention may share at least 90% sequence identity, such as at least 95%, 96%, 97%, 98% or 99% sequence identity (% SI) to SEQ ID NO: 5. This sequence has 100% homology with base pairs 1093 to 1684 of the Woodchuck hepatitis B virus (WHV8) genome.

The WPRE sequence may be truncated as long as it is functional, and a truncated WPRE sequence may comprise at least 525, 545, 555, 565, 575, or 585 (out of 593) bases and share at least 90%, such as at least 95%, 96%, 97%, 98% or 99% sequence identity (% SI) to SEQ ID NO: 5.

In one embodiment, the WRPE has a sequence corresponding to SEQ ID NO:5 or a sequence having at least 90% sequence identity, such as at least 95%, 96%, 97%, 98% or 99% sequence identity (% SI) to SEQ ID NO: 5.

Bovine Growth Hormone Poly-Adenylation (BGHpA) Signal Sequence

The vector may also incorporate a bovine growth hormone poly-adenylation (BGHpA or bGH-polyA) signal sequence. The BGHpA signal sequence is a 3'-flanking sequence ensuring efficient and accurate polyadenylation of the transgene transcripts (Goodwin and Rottman, 1992). The two major functions are to terminate DNA transcription and to protect the 3' end of the transcribed RNA against degradation in addition to RNA trafficking from the nucleus to the ribozomes. Thus the BGHpA signal sequence is located as the second last element in the vector, just upstream of the ITR sequence at the 3'-end.

Thus, in one embodiment, the (bGH-polyA) signal sequence is located downstream of said coding sequences for NPY and NPY2R.

The BGHpA signal sequence in the vector may share at least 90% sequence identity, such as at least 95%, 96%, 97%, 98% or 99% sequence identity (% SI) to SEQ ID NO: 6.

The BGHpA signal sequence may be truncated as long as it is functional, and a truncated BGHpA signal sequence may comprise at least 225, 235, 245, 255, or 265 (out of 269) bases and share at least 90% sequence identity, such as at least 95%, 96%, 97%, 98% or 99% sequence identity (% SI) to present in SEQ ID NO: 6.

In one embodiment, the BGHpA signal have a sequence corresponding to SEQ ID NO:6 or sequence a sequence having at least 90%, such as at least 95%, 96%, 97%, 98% or 99% sequence identity (% SI) to SEQ ID NO: 6.

Vector Summary

Taken together, the specific choices with regards to promoters and enhancer elements, cis-acting elements, as well as, transgene orientation and bicistronic elements, two resulting designs were selected according to an exemplary embodiment:

```
ITR-CAG-NPY-IRES-NPY2R-WPRE-BGHpA-ITR

ITR-CAG-NPY2R-IRES-NPY-WPRE-BGHpA-ITR
```

Thus, in one embodiment, the vector comprises the functional elements of AAV2 Inverted Terminal Repeat sequences (ITR), hybrid cytomegalovirus enhancer/chicken beta-actin CAG promoter (CAG), internal ribosome entry site (IRES), woodchuck hepatitis post-translational regulatory element (WPRE), and bovine growth hormone polyadenylation (BGHpA) signal sequence.

In one further embodiment, the sequences of the functional elements of the vector are operably linked and in the order of (upstream to downstream), 5'-ITR, CAG, NPY, IRES, NPY2R, WPRE, BGHpA, and ITR-3',
or
5'-ITR, CAG, NPY2R, IRES, NPY, WPRE, BGHpA, and ITR-3'.

A full sequence vector will also contain a number of bases between the functional elements, and two such full sequences were put together according to an exemplary embodiment. In one embodiment, the vector has a sequence corresponding to SEQ ID NO: 9 or sequence a sequence having at least 90% sequence identity, such as at least 95%, 96%, 97%, 98% or 99% sequence identity (% SI) to SEQ ID NO: 9, or the vector has a sequence corresponding to SEQ ID NO: 10 or a sequence having at least 90% sequence identity, such as at least 95%, 96%, 97%, 98% or 99% sequence identity (% SI) to SEQ ID NO: 10.

The vector sequence(s) may be truncated as long as it is functional, and a truncated vector sequence(s) may comprise at least 4200, such as 4230, 4260, 4270, 4280 (out of 4288) bases and share at least 90% sequence identity, such as at least 95%, 96%, 97%, 98% or 99% sequence identity (% SI) to SEQ ID NO: 9, or the a truncated vector sequence(s) may comprise at least 4200, such as 4230, 4260, 4270, 4280 (out of 4288) bases and share at least 90% sequence identity, such as at least 95%, 96%, 97%, 98% or 99% sequence identity (% SI) to SEQ ID NO: 10.

The vector can also be described in the intra vector ranges, such as the distances between the promoter or internal ribosome entry site sequences and the NPY and/or NPY2R coding sequences. The total size of the vector is also a consideration, since AAV has a packaging capacity of ~4.7K.

In one embodiment, the distance between the CAG promoter sequence and the coding sequence for NPY or NPY2R being downstream of the CAG promoter sequence and upstream of the IRES sequence, is in the range of 60 to 0 bases, preferably 40 to 5 bases, most preferably 20 to 10 bases.

In one embodiment, the distance between the IRES sequence and downstream coding sequence for NPY or NPY2R is in the range of 60 to 0 bases, preferably 40 to 2 bases, most preferably 10 to 4 bases.

As know in the art, several tools exist for gene optimization, taking advantage of the degeneracy of the genetic code. Because of degeneracy, one protein can be encoded by many alternative nucleic acid sequences. Codon preference differs in each organism, and this might create challenges for expressing recombinant proteins in heterologous expression systems, resulting in low and unreliable expression. This may also be true for autologous expression, where wild type sequences may not be optimized for expression yield but also for degradation, regulation, and other properties. Thus the vector can be optimized for human expression using a large number of sequence-related parameters involved in different aspects of gene expression, such as transcription, splicing, translation, and mRNA degradation.

Thus in one embodiment, the sequence of the vector has been codon optimized for use in humans.

AAV Particle Generation

As further described in the experimental section, the vectors are packed in capsid proteins of serotype 1, 2, or 8. Thus, from the two vectors (above), six different AAV particles can be generated, as summarized below:

```
AAV2.1-ITR-CAG-NPY-IRES-NPY2R-WPRE-BGHpA-ITR

AAV2.1-ITR-CAG-NPY2R-IRES-NPY-WPRE-BGHpA-ITR

AAV2.2-ITR-CAG-NPY-IRES-NPY2R-WPRE-BGHpA-ITR

AAV2.2-ITR-CAG-NPY2R-IRES-NPY-WPRE-BGHpA-ITR
```

-continued

```
AAV2.8-ITR-CAG-NPY-IRES-NPY2R-WPRE-BGHpA-ITR

AAV2.8-ITR-CAG-NPY2R-IRES-NPY-WPRE-BGHpA-ITR
```

Thus in one embodiment, an AAV particle comprises a vector of the invention is encapsulated by Adeno-associated virus (AAV) capsid proteins, packaged in so-called pseudotyped AAV particles, meaning that they are coated with capsid proteins from different AAV serotypes.

AAV Particle Delivery

The delivery of the NPY and NPY2R gene therapy should preferably be via site-specific intracranial injections of the AAV particles containing the vector. A pharmaceutical composition comprising the AAV particle is used in the prevention, inhibition, amelioration, or treatment of a neurological disorder in a mammal, such as epilepsy or Parkinson's disease. The primary target is pharmacoresistant (intractable, refractory, medical intractable, drug resistant) epilepsy, since for these forms of epilepsy, few treatment effective methods exist. Pharmacoresistant epilepsy includes a wide spectrum of types of epilepsy where pharmaceutical treatment has no effect, or where there is variability over time in the pharmaceutical treatment results. In very broad and general terms, pharmacoresistance can be said to be failure of seizures to come under complete control or acceptable control in response to anti epileptic drug (AED) therapy.

In one embodiment, a pharmaceutical composition comprises the AAV particle for use in the prevention, inhibition, amelioration, or treatment of a neurological disorder in a mammal such as epilepsy or Parkinson's disease. In one further embodiment, said neurological disorder is epilepsy. In one further embodiment, said epilepsy is pharmacoresistant epilepsy. In one further embodiment, the subject is a mammalian subject, such as a human, horse, dog or cat subject. In one further embodiment, the subject is a human subject. In one further embodiment, the neurological disorder is Epilepsy and the composition comprises and the composition comprises AAV1-NPY/Y2, AAV1-Y2/NPY, AAV2-NPY/Y2, AAV2-Y2/NPY, AAV8-NPY/Y2, or AAV8-Y2/NPY particles, such as AAV1-NPY/Y2, AAV1-Y2/NPY, or AAV8-NPY/Y2 particles, such as AAV1-NPY/Y2 particles. In one further embodiment, the neurological disorder is Parkinson's disease and the composition comprises AAV1-NPY/Y2, AAV1-Y2/NPY, AAV2-NPY/Y2, AAV2-Y2/NPY, AAV8-NPY/Y2, or AAV8-Y2/NPY particles, preferably AAV1-NPY/Y2, AAV1-Y2/NPY, or AAV8-NPY/Y2 particles, preferably AAV1-NPY/Y2 particles.

A hallmark of Parkinson's disease is the loss of dopamine neurons in the substantia nigra projecting to the striatum leading to a loss in dopamine release in the striatum. This results in a decrease of dopaminergic transmission and abnormal downstream firing within the basal ganglia circuits, which gives rise to rigidity and cataleptic symptoms. NPY counteracts this depression of dopaminergic transmission by promoting the synthesis and release of dopamine through Y2 receptor activation, while activation of the Y1 receptor has an opposite effect (Adewale et al., 2005, 2007). Moreover, NPY exerts Y2-mediated neuroprotective effects on dopaminergic neurons against 6-hydroxydopamine (6-OHDA)-induced toxicity both in vitro and in vivo (Decressac et al., 2011, 2012). Moreover, post-mortem brains from Parkinson's disease patients exhibit an increased number of NPY-positive cells in the caudate nucleus and putamen as compared to healthy controls (Cannizzaro et al., 2003), which might reflect an endogenous, but sequentially insufficient neuroprotective response. This is consistent with dopaminergic neurons in the striatum and substantia nigra expressing functional Y2 receptors (Shaw et al., 2003), and an increased number of NPY-positive neurons in the striatum and nucleus accumbens after striatal 6-OHDA-induced loss of dopaminergic neurons (Kerkerian-Le Goff et al., 1986; Salin et al., 1990).

In one further embodiment, said neurological disorder is Parkinson's disease. The gene therapy could also be delivered systemically relying on AAV serotype tissue tropism; however, by intracranial injection a precise targeting to the diseased brain region with high efficacy and minimal side effects is obtained. In this way the viral vector will be contained within a defined region with expected minimal spread to surrounding areas along white matter tracts. Depending on the type of neurological disorder the AAV delivery approach could be either to very confined brain regions or if appropriate a delivery covering larger areas of the cerebral cortex. Depending on the type of epilepsy and the location of the epileptic focus or foci, the AAV delivery approach could be either to very confined brain regions or if appropriate a delivery covering larger areas of the cerebral cortex. Thus, several possible administration methods exist, such as intracerebroventricular, intravitreal, intravenous, subcutaneous, intramuscular, intranasal, transmucosal, intracerebral, intraperitoneal, intrathecal, intraarterial administration.

In one embodiment, a pharmaceutical composition comprising the AAV particles is delivered through site-specific intracranial injections.

All AAV serotypes of the invention have been proven capable of transducing glia cells and neurons. AAV2 serotypes have shown smaller spreading of the vector and a natural occurring neuronal tropism, why a vector with AAV2 serotype capsid proteins may be suitable delivery to smaller and more defined brain regions. Similarly, vectors with AAV1 or AAV8 serotype capsid proteins may be suitable delivery covering larger areas of the cerebral cortex.

The dose of AAV particles may consist of one dose, or several doses given at one or multiple occasions. The single dose has the advantage of avoiding multiple intracranial injections, while multiple doses may enable the use of a lower dose for each injection, while monitoring patient dose response between injections. Typically, the dose may range between 0.01 to 100 µg, such as 0.1-50 µg or 0.5-20 µg of the functional AAV particle. Transduction efficacy may also be affected by other factors, such as the position of the subjects during and after injection, to facilitate spreading of the vector.

In one embodiment, an effective dose of the functional AAV range between 0.01 to 100 µg, such as 0.1-50 µg or 0.5-20 µg of the functional AAV particle. In one further embodiment, the AAV particle is formulated for administration as a single dose or multiple doses, such as two, three, four, five doses.

In one embodiment, a method for treating, inhibiting, or ameliorating a neurological disorder in a subject, comprises administering into cells of the central nervous system of a subject suffering from a neurological disorder, a pharmaceutically effective amount of such a composition. In one further embodiment, the subject is a mammalian subject, such as a human subject. Furthermore, the neurological disorder is Epilepsy or Parkinson's disease. In the method, the composition is delivered through site-specific intracranial injections, and in one further embodiment, the neurological disorder is Epilepsy and the composition is delivered to the location of the epileptic focus or foci.

The delivery of the NPY and NPY2R could also be to cells, such as endogenous cells from a subject, by delivery of the AAV particles containing the vector to said cells. In turn, such cells could be administered, such as by being injected or migrating into a site in a subject, for the prevention, inhibition, amelioration, or treatment of a neurological disorder in a mammal such as epilepsy or Parkinson's disease such as seen in ex vivo gene therapeutic approaches with subsequent grafting of the cells infected or transduced by the AAV vectors. Such a subject could be a mammal, such as a human subject.

In one embodiment, a method of delivery of an NPY and Y2 genome to a mammalian cell, comprises introducing into a cell said AAV particle. In one further embodiment, the cell is selected from the group consisting of a neural cell, lung cell, retinal cell, epithelial cell, muscle cell, pancreatic cell, hepatic cell, myocardial cell, bone cell, spleen cell, keratinocyte, fibroblast, endothelial cell, prostate cell, germ cell, progenitor cell, and a stem cell. In one embodiment, a method of administering an NPY and Y2 genome to a subject comprises administering said cell (comprising the NPY and Y2 genome) to the subject. In one embodiment, the subject is a mammalian subject, such as a human subject.

In one embodiment, a method of delivery of an NPY and Y2 genome to a subject comprises administering to a mammalian cell in a subject a said AAV particle, wherein the virus particle is administered to the hippocampus of the subject.

In one embodiment, a method of delivery of an NPY and Y2 genome to a subject comprises administering to a mammalian cell in a subject a said AAV particle, wherein the virus particle is administered to the striatum, the nucleus accumbens, the substantia nigra, the ventral tegmental area, or the medial forebrain bundle of the subject.

The delivery of the NPY and NPY2R could also be for reducing a disease where NPY and/or NPY2R activation has a therapeutic effect or is caused by NPY-deficiency, wherein the disease is selected from Epilepsy and Parkinson's disease. Thus, in one embodiment, a method of reducing a disease where NPY has a therapeutic effect or is caused by NPY-deficiency, wherein the disease is selected from Epilepsy and Parkinson's disease, comprises administering into cells of the central nervous system of a subject suffering from a neurological disorder, a pharmaceutically effective amount of said composition.

In one embodiment, a method of providing NPY to a subject in need thereof comprises selecting a subject in need of NPY, such as a subject with an NPY deficiency and providing said subject a pharmaceutically effective amount of said composition. In one further embodiment, said subject is selected as one having an NPY deficiency by clinical evaluation or diagnostic test, such as e.g., EEG and/or clinical diagnosis of epilepsy or Parkinson's disease.

Evaluation of Transgene Expression

The vectors of the invention were tested for their ability to initiate expression of NPY and NPY2R. Transient transfection of HEK293 cells with AAV expression plasmids including sequences for NPY and NPY2R resulted in increased levels of the mRNA transcript encoding both transgenes, as measured by elevated amounts of both the NPY and Y2 target sequences in duplex ddPCR reactions, as can be seen in FIG. 2. For both plasmids, the expression levels of the target sequence for the transgene upstream of the IRES was more abundant than the target sequence for the downstream transgene.

NPY and NPY2R Expression in Hippocampus

Figure 3:
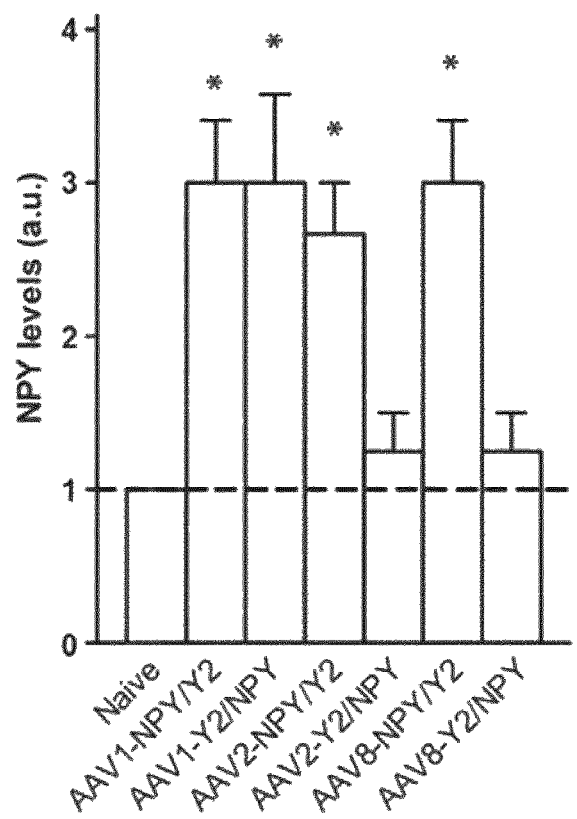
FIG. 3 shows a graph illustrating NPY expression in hippocampal slices from rats. NPY levels in the CA1 region of the dorsal hippocampus three weeks after unilateral AAV vector treatment. NPY levels were evaluated corresponding to the observed NPY-positive immunofluorescence signal: 1 (NPY levels corresponding to endogenous levels), 2 (low NPY expression above the endogenous level), 3 (moderate NPY expression above the endogenous level), and 4 (high NPY expression above the endogenous level). Data are presented as mean values±s.e.m and analyzed using Mann-Whitney U test. *P<0.05 as compared to untreated naïve control animals.
Figure 4:
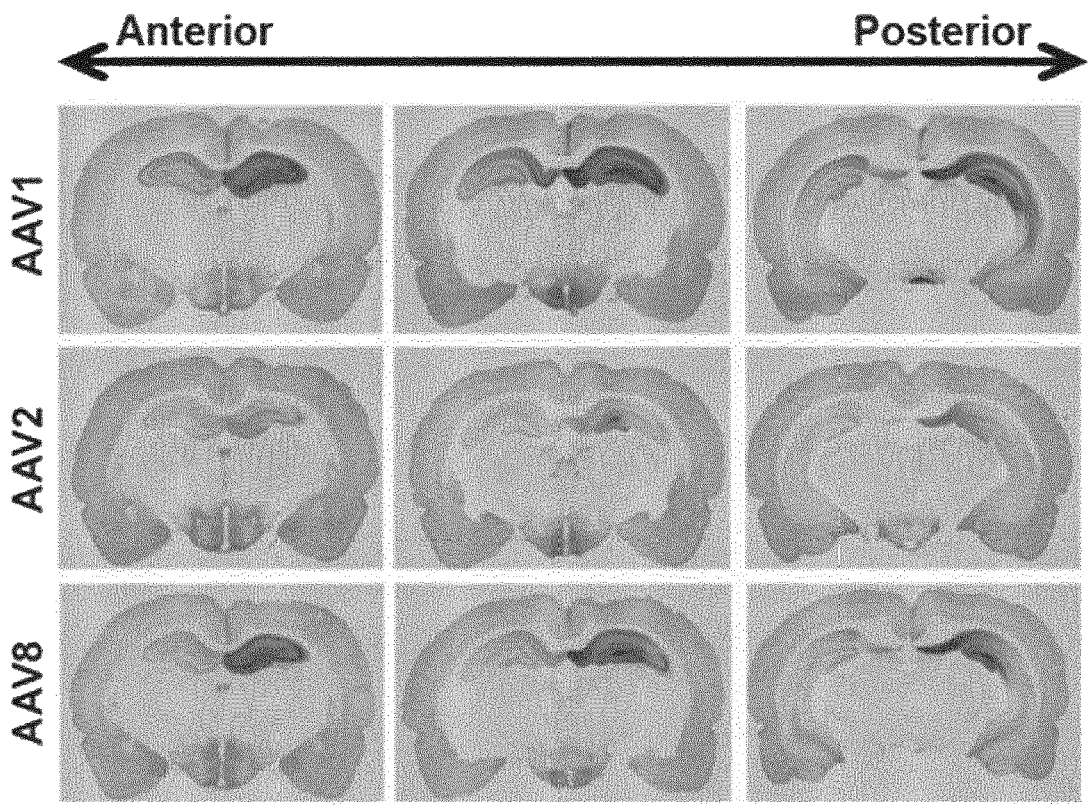
FIG. 4 shows images illustrating NPY expression in the dorsal hippocampus three weeks after unilateral AAV-NPY/Y2 vector treatment. The darker the DAB-staining the higher NPY-like immunoreactivity levels. Rats treated with AAV-Y2/NPY vectors (not shown) had NPY expression corresponding to 9-17% of the expression seen in the figure.
Figure 5A:
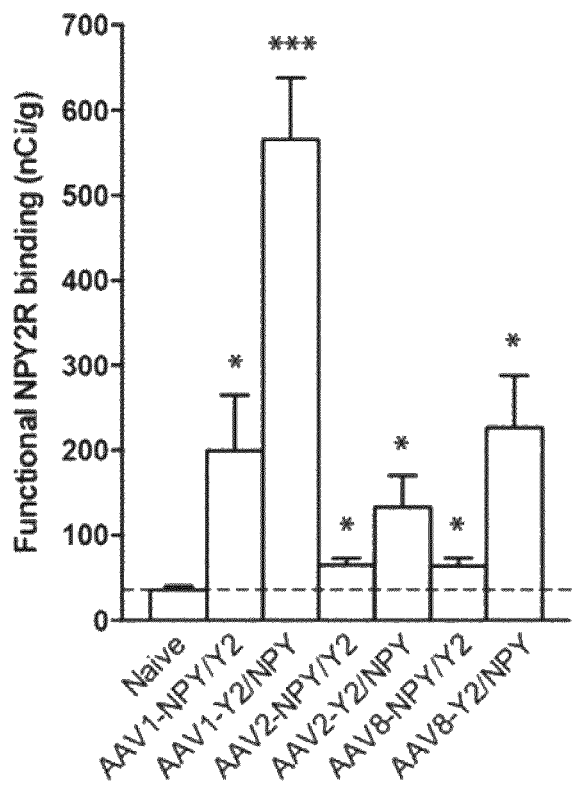
FIG. 5A and 5B illustrates NPY2R functionality in hippocampal slices from rats, where 5A shows a graph illustrating levels of functional NPY2R binding in the CA1 region of the dorsal hippocampus three weeks after unilateral AAV vector treatment. Data are presented as mean values±s.e.m and analyzed using unpaired two-tailed Student's t-test. *P<0.05, ***P<0.001 as compared to untreated naïve control animals. 5B shows representative images of the functional NPY2R binding shown in A.
Figure 5B:
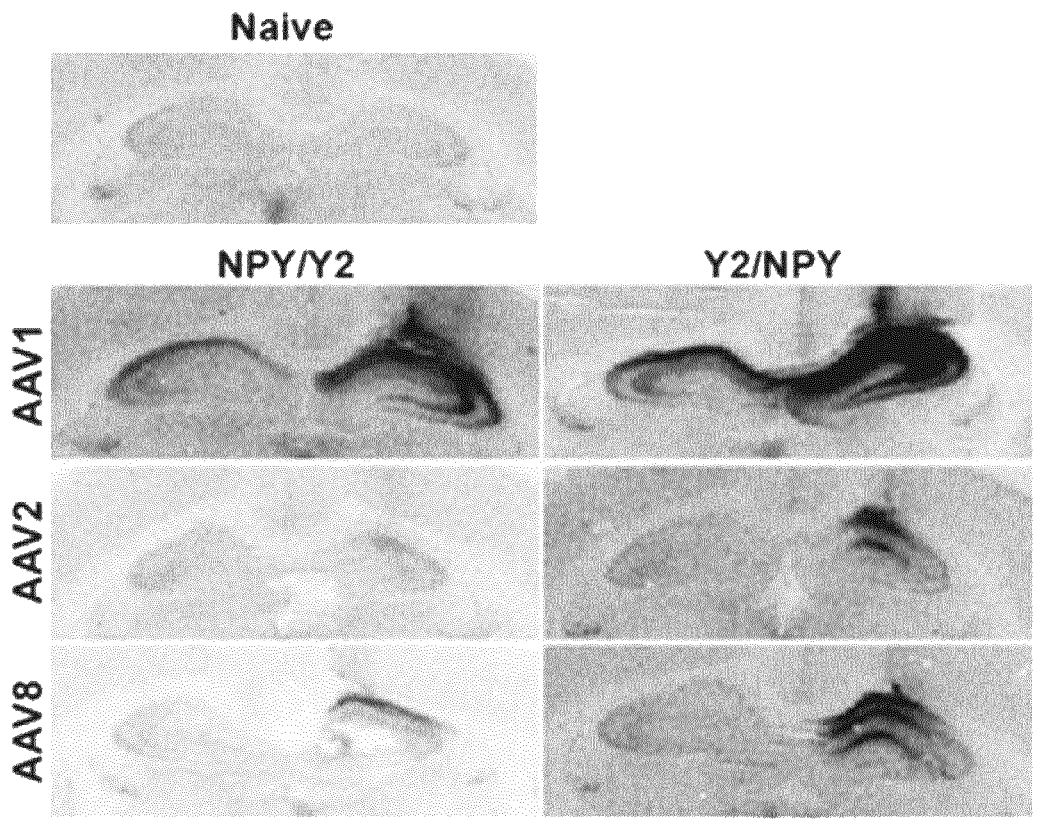
Figure 6A:
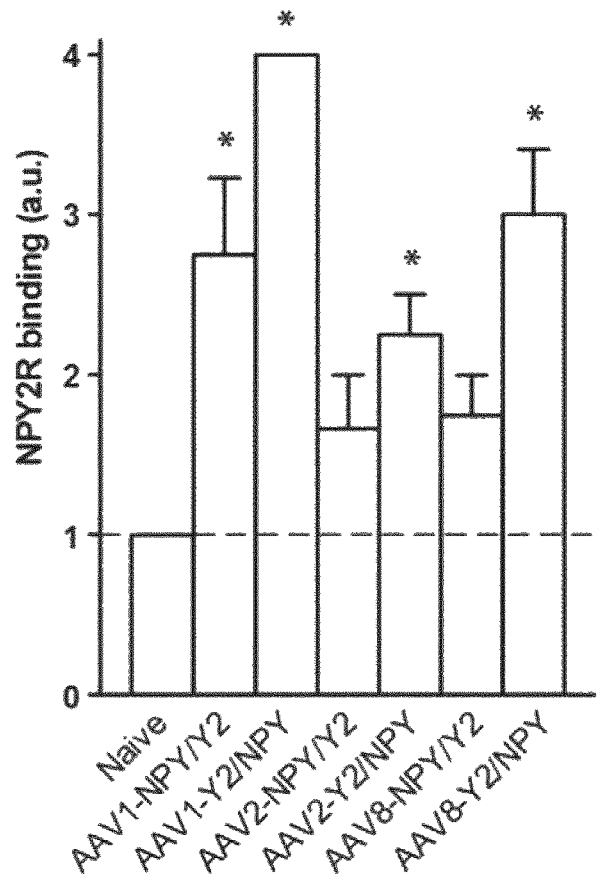
FIG. 6 illustrates NPY2R expression in hippocampal slices from rats, where 6A shows a graph illustrating levels of NPY2R binding in the dorsal hippocampus three weeks after unilateral AAV vector treatment. Y2 receptor binding was evaluated in the hippocampal CA1 region and given values corresponding to the Y2 receptor signal: 1 (Y2 receptor expression corresponding to endogenous levels), 2 (low Y2 receptor expression above the endogenous level), 3 (moderate Y2 receptor expression above the endogenous level), and 4 (high Y2 receptor expression above the endogenous level). Data are presented as mean values±s.e.m and analyzed using Mann-Whitney U test. *P<0.05 as compared to untreated naïve control animals. 6B shows representative images of the functional NPY2R binding shown in 6A.
Figure 6B:
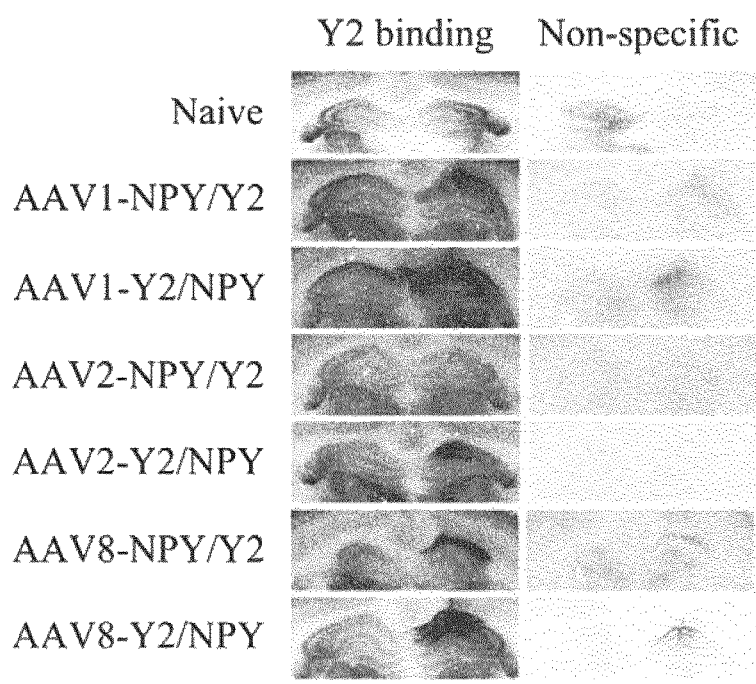

After experimentally validating the sequences of the AAV expression plasmids, including the NPY and NPY2R sequences, the plasmids were packaged in AAV capsid particles of AAV serotype 1, 2, or 8 origin, generating a total of 6 unique AAV vector particles, as described above. These particles were purified and progressed for in vivo testing in rats. Three weeks after intracranial injections in the dorsal hippocampus of adult male Wistar rats, the animals were euthanized and their brains were collected and snap-frozen. Subsequently, brain slices from these brains were subjected to evaluation of transgene expression of NPY and NPY2R using immunohistochemical assays targeting NPY as well as autoradiography assays visualizing NPY2R-binding and GPCR functional binding. Treatment with AAV1-NPY/Y2, AAV1-Y2/NPY, AAV2-NPY/Y2, or AAV8-NPY/Y2 all resulted in significantly increased NPY levels (FIGS. 3 and 4). The hierarchical order of the AAV vectors to induce NPY expression was as follow: AAV1-NPY/Y2=AAV1-Y2/NPY=AAV8-NPY/Y2>AAV-NPY/Y2>AAV8-Y2/NPY=AAV2-Y2/NPY. All six vectors resulted in increased functional NPY2R levels (FIGS. 5A and 5B) and significantly increased NPY2R binding levels were also observed after treatment with AAV1-NPY/Y2, AAV1-Y2/NPY, AAV2-Y2/NPY, or AAV8-Y27NPY (FIGS. 6A and 6B). The hierarchical order of the AAV vectors to induce NPY2R expression was as follow: AAV1-Y2/NPY>AAV8-Y2/NPY=AAV1-NPY/Y2>AAV2-Y2/NPY>AAV8-NPY/Y2=AAV2-NPY/Y2.

Thus, both AAV expression plasmids (AAV-NPY/Y2 and AAV-Y2/NPY) were successfully transcribed and resulted in expression of NPY and NPY2R protein. Furthermore, in all cases the level of transgene expression depended on the transgene sequence being located upstream or downstream of the IRES sequence, with the transgene located upstream of the IRES sequence being expressed at relative higher levels than the transgene located downstream of the IRES sequence.

AAV vectors pseudotyped with capsid proteins from AAV serotype 1 had the highest transgene expression efficacy (AAV1>AAV8>AAV2) when injected intracranially into the rat hippocampus. Thus, in one embodiment, the AAV capsid proteins of the AAV particle are selected from the group consisting of AAV1, AAV2 and AAV8, preferably AAV1 and AAV8.

Surprisingly, it was found that AAV vectors pseudotyped with capsid proteins from AAV serotype 1 showed a very high expression of the transgene located downstream of the IRES element (as can be seen in FIGS. 4A and 4B), compared to the other AAV vectors pseudotyped with capsid proteins from AAV serotype 2 and 8, which showed a relative lower expression for the downstream transgene. Thus the AAV vectors pseudotyped with capsid proteins from AAV serotype 1 show a high expression for the first and second transgene (i.e. NPY and NPYR2).

One of the bigger obstacles for clinical AAV gene therapy is to ensure safe expression with high efficacy. Thus the homogeneously high expression is deemed very positive. Thus in one embodiment, the AAV capsid proteins of the AAV particle are selected from the group consisting of AAV1, AAV2 and AAV8, most preferably AAV1. In one further embodiment, the AAV particle has AAV1 capsid proteins for a more homolog overexpression of both transgenes (NPY and NPY2R).

In contrast, in such cases where heterologus expression efficacy for the NPY and NPY2R transgenes is desired, AAV vectors pseudotyped with capsid proteins from AAV serotype 2 and 8 presents may be preferable.

According to an embodiment, sequence identity (% SI) as used herein may be assessed by any convenient method. It is common practice to use computer programs will be employed for such calculations, and the suite of standard programs for comparing and aligning pairs of sequences include ALIGN (Myers and Miller, *CABIOS*, 4:11-17, 1988), FASTA (Pearson, *Methods in Enzymology*, 183:63-98, 1990) and gapped BLAST (Altschul et al., *Nucleic Acids Res.*, 25:3389-3402, 1997), or BLASTP (Devereux et al., *Nucleic Acids Res.*, 12:387, 1984). If no such resources are at hand, according to one embodiment, sequence identity (% SI) can be calculated as (% SI)=100%*(Nr of identical residues in pairwise alignment)/(Length of the shortest sequence).

The expression results can further be analysed using scoring, as shown in tables 1 to 3. In table 1, the transgene expression was scored per serotype.

TABLE 1

Table 1: Transgene expression from the AAV1, AAV2, or AAV8 vectors

| AAV vector serotype | NPY expression | | NPY2R expression | |
| --- | --- | --- | --- | --- |
| | NPY protein levels (1-4) | Ranking (1-3) | NPY2R protein Levels (1-4) | Ranking (1-3) |
| AAV1 | 3.0 ± 0.3 | 1 | 3.3 ± 0.4 | 1 |
| AAV2 | 1.9 ± 0.3 | 3 | 2.0 ± 0.2 | 3 |
| AAV8 | 2.1 ± 0.4 | 2 | 3.4 ± 0.3 | 2 |

Table 1 shows NPY and NPY2R protein levels in animals treated with NPY and Y2 overexpressing AAV1, -2, and -8 vectors. Protein levels were evaluated corresponding to the observed NPY or NPY2R protein signal: 1 (protein levels corresponding to endogenous levels), 2 (low protein expression above the endogenous level), 3 (moderate protein expression above the endogenous level), and 4 (high protein expression above the endogenous level). Data are presented as mean values±s.e.m. Subsequently the different AAV vectors are giving a rank from 1-3, with 1 being equivalent to the highest expression levels and 3 being equivalent to lowest.

Thus it is clear that AAV vectors pseudotyped with capsid proteins from AAV serotype 1 had the highest transgene expression efficacy (AAV1>AAV8>AAV2) when injected intracranially into the rat hippocampus.

Furthermore, transgene expression can also be evaluated with regards to the two vector orientations (NPY/Y2 or Y2/NPY), as shown in table 2.

TABLE 2

Table 2: Transgene expression from the NPY/Y2 or Y2/NPY vectors

| Transgene orientation | NPY expression | | NPY2R expression | |
| --- | --- | --- | --- | --- |
| | NPY protein levels (1-4) | Ranking (1-2) | NPY2R protein Levels (1-4) | Ranking (1-2) |
| NPY/Y2 | 2.9 ± 0.2 | 1 | 2.1 ± 0.3 | 2 |
| Y2/NPY | 1.8 ± 0.3 | 2 | 3.0 ± 0.3 | 1 |

Table 2 shows NPY and NPY2R protein levels in animals treated with NPY/Y2 or Y2/NPY AAV vectors. Protein levels were evaluated corresponding to the observed NPY or NPY2R protein signal: 1 (protein levels corresponding to endogenous levels), 2 (low protein expression above the endogenous level), 3 (moderate protein expression above the endogenous level), and 4 (high protein expression above the endogenous level). Data are presented as mean values±s.e.m. Subsequently the different AAV vectors are giving a rank from 1-2, with 1 being equivalent to the highest expression levels and 2 being equivalent to lowest.

Thus it is clear that the level of transgene expression depended on the transgene sequence being located upstream or downstream of the IRES sequence, with the transgene located upstream of the IRES sequence being expressed at relative higher levels than the transgene located downstream of the IRES sequence.

AAV Vector-Mediated Effects on KA-Induced Seizures

Figure 7A:
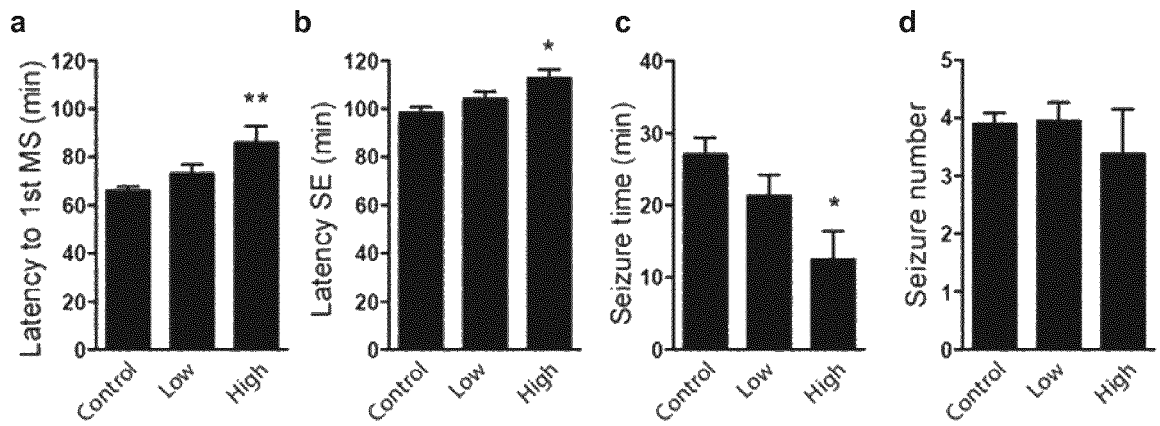
FIG. 7A shows the relationship between seizure development and AAV-induced NPY transgene overexpression. Control: NPY levels corresponding to endogenous levels (corresponding to the value 1 in FIG. 3); Low: Low NPY transgene expression levels (corresponding to the value 2 in FIG. 3); High: High NPY transgene expression levels (corresponding to the values 3-4 in FIG. 3). a) Latency to first motor seizure (MS), b) Latency to status epilepticus (SE), and c) Seizure time were all significantly different in treated rats with high transgene NPY expression, indicating anti-seizure effects, as compared to rats with NPY expression equal to endogenous levels. d) Seizure numbers were unaffected in all categories.
Figure 7B:
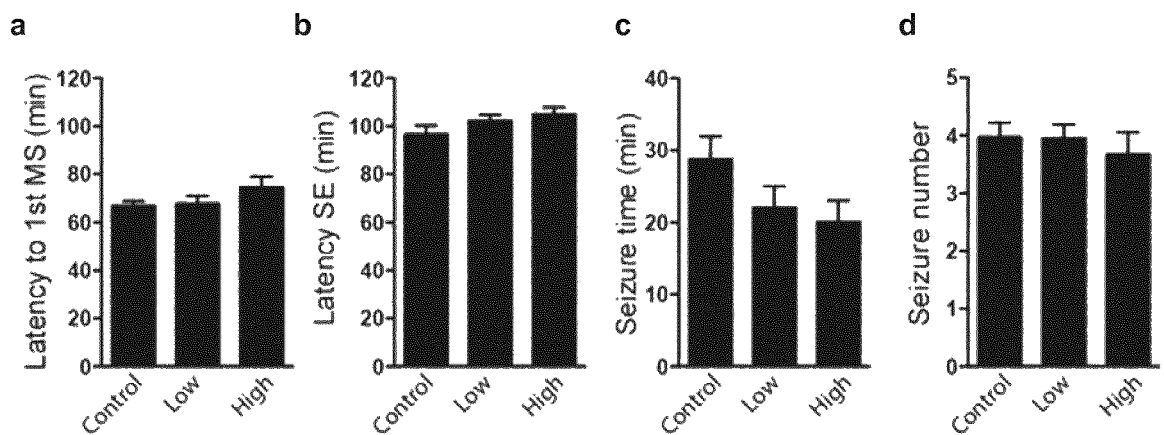
FIG. 7B shows the relationship between seizure development and AAV-induced NPY2R (Y2) transgene overexpression. Control: NPY2R levels corresponding to endogenous levels (corresponding to the value 1 in FIG. 3); Low: Low NPY2R transgene expression levels (corresponding to the value 2 in FIG. 3); High: High NPY2R transgene expression levels (corresponding to the values 3-4 in FIG. 3). a) Latency to first motor seizure (MS), b) Latency to status epilepticus (SE), c) Seizure time, and d) seizure number were not significantly altered in any of the NPY2R expression categories. However, strong tendencies were observed, especially for a decrease in c) Seizure time in the category High NPY2R expression. Data are presented as mean values±s.e.m and analyzed using Bonferroni's multiple comparison post-hoc tests following significant one-way ANOVA. *P<0.05, **P<0.01.

Kainate-induced seizure model in rats was used to evaluate the seizure-inhibitory effects of AAV vector-mediated expression of NPY and its receptors. This model is believed to reflect the acute seizure events in temporal lobe epilepsy including measurement of latency times to first motor seizure and status epilepticus as well as frequency and duration of seizures and a general modified seizure severity score. This is illustrated in FIG. 7, which shows a graphic illustration of the seizure development during a 2 hours period observation after a single kainate injection (s.c.) in relationship to the levels of AAV-induced transgene overexpression. High levels of AAV vector-induced NPY expression levels resulted in increased latencies to both $1s^t$ motor seizure and status epilepticus as well as decreased time spent in seizures, as compared to endogenous and lower levels of NPY expression (FIG. 7A). High levels of AAV vector-induced NPY2R expression levels resulted in tendencies, however not reaching significant levels, decreased time spent in seizures, as compared to endogenous and lower levels of NPY2R expression (FIG. 7B).

Figure 8A:
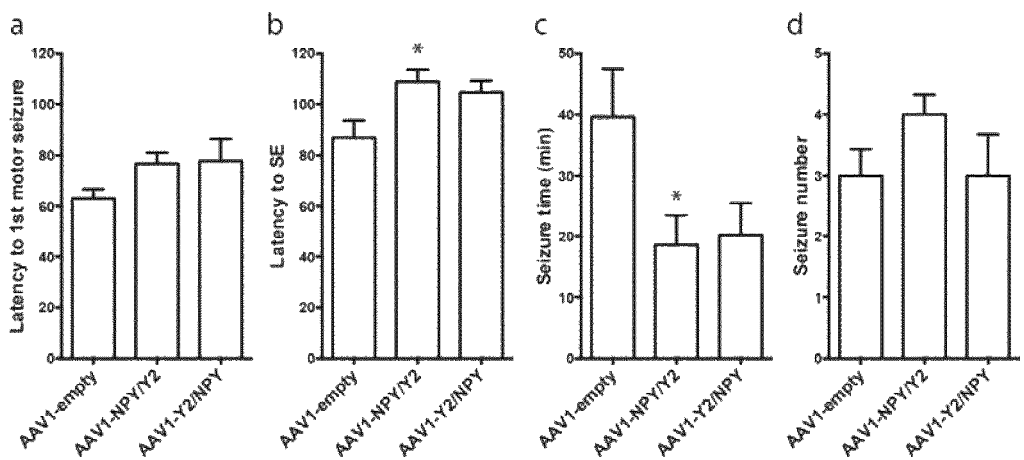
FIG. 8 illustrates effects of bilateral intrahippocampal AAV vector injections on KA-induced seizures: 8A shows the effects of bilateral intrahippocampal AAV1 vector injections on KA-induced seizures. a) Latency to first motor seizure and d) total number of seizures were not affected after AAV1 vector mediated NPY and Y2 overexpression as compared to control (AAV1-empty). b) Latency to status epilepticus (SE) and c) Total seizure time were both significantly decreased after AAV1-NPY/Y2 treatment as compared control (AAV1-empty), whereas AAV1-Y2/NPY were without significant effects. Data are mean±SEM (n=7-8 in each group). *P<0.05 versus control (AAV1-empty), Bonferroni's multiple comparison post-hoc tests following significant one-way ANOVA. 8B shows the effects of bilateral intrahippocampal AAV2 vector injections on KA-induced seizures. No effects on KA-induced seizures were observed after AAV2 vector-mediated NPY and Y2 overexpression. This included observations of a) Latency to first motor seizure, b) Latency to status epilepticus (SE), c) Total seizure time, and d) total number of seizures. Data are mean±SEM (n=8 in each group). Bonferroni's multiple comparison post-hoc tests following significant one-way ANOVA. 8C shows the effects of bilateral intrahippocampal AAV8 vector injections on KA-induced seizures. No effects on KA-induced seizures were observed after AAV8 vector-mediated NPY and Y2 overexpression. This included observations of a) Latency to first motor seizure, b) Latency to status epilepticus (SE), c) Total seizure time, and d) total number of seizures. Data are mean±SEM (n=8-12 in each group). Bonferroni's multiple comparison post-hoc tests following significant one-way ANOVA.

In FIG. 8A, it can further be seen that treatment with AAV1-NPY/Y2 increased latency to development of status epilepticus (SE) and decreased total seizure time whereas the effects observed after AAV1-Y2/NPY treatment did not show statistical significance, as compared to AAV1-empty treatment (FIG. 8A). Both AAV1-NPY/Y2 and AAV1-Y2/NPY did not affect latency to first motor seizure or the total number of seizures (FIG. 8A).

Figure 8B:
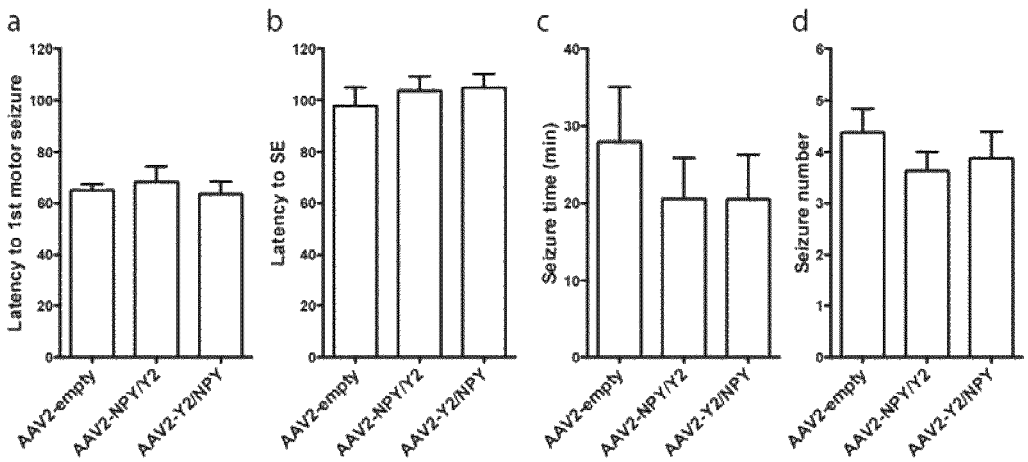

As can be seen in FIG. 8B, treatment with AAV2-NPY/Y2 or AAV2-Y2/NPY did not result in any significant changes in seizure development or severity as compared to AAV2-empty (FIG. 8B).

Figure 8C:
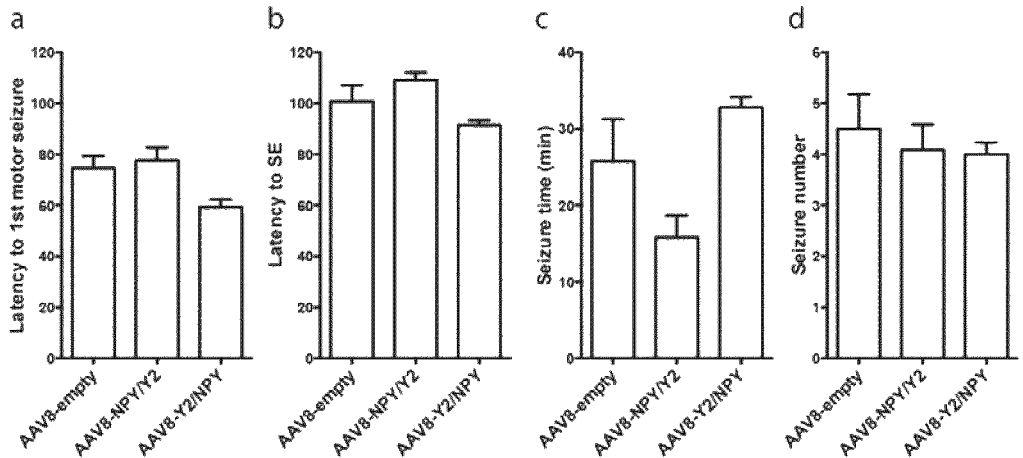

As can be seen in FIG. 8C, treatment with AAV8-NPY/Y2 did show increased latency to development of status epilepticus (SE) and decreased total seizure time whereas no significant effects were observed for AAV8-Y2/NPY, compared to AAV8-empty (FIG. 8C). However, a strong though not significant tendency to AAV8-NPY/Y2-induced decrease in total seizure time was observed (FIG. 8C).

Of all the vector particles, it was found that treatment with AAV1-NPY/Y2 resulted in anti-seizure effects as evident by the observed decreased seizure duration and increased latency time to development of SE. Treatment with AAV1-Y2/NPY, AAV2-NPY/Y2, AAV2-Y2/NPY, AAV8-NPY/Y2, or AAV8-Y2/NPY did not result in statistically significant inhibition of seizure development or severity. The spread and NPY transgene expression efficacy of the AAV vector particles was found to be serotype dependent (AAV1>AAV8>AAV2). Transgene expression of NPY and Y2 was confirmed by NPY immunostaining and functional Y2 receptor binding assays, respectively. No abnormal behavior or apparent health issues were observed in the animals following the intracranial injections and the AAV vector treatment.

In summary, FIG. 8 illustrates that AAV1-NPY/Y2, AAV1-Y2/NPY, AAV8-NPY/Y2 show a clear trend of anti-seizure effects as evident by the observed decreased seizure duration and increased latency time to development of SE, for AAV1-NPY/Y2 with clear statistical significance. The results are less clear for the AAV2 constructs, and neither did AAV8-Y2/NPY show a clear trend of anti-seizure effects. It is clear for in vivo systems, that although expression does not equal efficacy, expression still is essential for the vector function.

By having the transgenes for NPY and NPY2R expressed from a single construct, the vectors of the invention give a never previously seen opportunity in an animal model to see both expression levels for NPY/NPY2R proteins correlated to medical effects. All transduced cells have been infected with constructs having an equal number of NPY and NPY2R genes where all transferred genes are localized in the same position, and where the ration of NPY/NPY2R is fixed and vector dependent (why the ratio will also be consistent for all transformed cells). The spread and distribution of the NPY and NPY2R genes will also not differ, but they will localize in the exact same cells. These effects are not possible to achieve using two vectors, containing and NPY and NPY2R gene respectively. Positive effects for this include a very consistent treatment result. Statistically, this also makes it easier to score each individual vector for its effects. By scoring the different qualities of the vectors (expression and efficacy in suppressing kainate-induced seizures), as shown in table 3, it becomes easier to highlight which vectors are most proficient for treatment.

TABLE 3

Table 3: Overall ranking of the AAV vectors

| AAV vector | Expression rank (1-6) | Efficacy rank (1-6) | Overall mean rank (1-6) |
|---|---|---|---|
| AAV1-NPY/Y2 | 2 | 2 | 1 |
| AAV1-Y2/NPY | 1 | 3 | 1 |
| AAV2-NPY/Y2 | 6 | 5 | 6 |
| AAV2-Y2/NPY | 5 | 4 | 4 |
| AAV8-NPY/Y2 | 3 | 1 | 1 |
| AAV8-Y2/NPY | 4 | 6 | 4 |

Table 3 shows overall ranking of the six AAV vectors based on both the transgene expression and efficacy as anti-seizure treatment in the acute kainate induced seizure model. Ranks are given from 1-6, with 1 being equivalent to the highest rank and 6 being equivalent to the lowest. Overall rank represents the mean rank of expression and efficacy ranking. Overall ranking is showing AAV1-NPY/Y2=AAV1-Y2/NPY=AAV8-NPY/Y2>AAV8-Y2/NPY=AAV2-NPY/Y2>AAV2-Y2/NPY.

Thus in one embodiment, the AAV particle is AAV1-NPY/Y2, AAV1-Y2/NPY, or AAV8-NPY/Y2. In one embodiment, the AAV particle is AAV1-NPY/Y2.

Treatment with AAV1-NPY/Y2, AAV1-Y2/NPY, AAV2-NPY/Y2, or AAV8-NPY/Y2 all resulted in significantly increased NPY levels (FIGS. 3 and 4). Treatment with all 6 vectors resulted in increased functional NPY2R levels (FIGS. 5A and 5B), although with highest expression for AAV1-Y2/NPY. NPY2R binding levels were increased for all 6 vectors, and significantly so after treatment with AAV1-NPY/Y2, AAV1-Y2/NPY, AAV2-Y2/NPY, or AAV8-Y2/NPY (FIGS. 6A and 6B).

The hierarchical order of the AAV vectors to induce NPY expression was as follow: AAV1-NPY/Y2=AAV1-Y2/NPY=AAV8-NPY/Y2>AAV-NPY/Y2>AAV8-Y2/NPY=AAV2-Y2/NPY. The hierarchical order of the AAV vectors to induce NPY2R expression was as follow: AAV1-Y2/NPY > AAV8-Y2/NPY=AAV1-NPY/Y2>AAV2-Y2/NPY >AAV8-NPY/Y2=AAV2-NPY/Y2. This suggests that a high NPY expression with a co-localized NPY2R expression seems favourable for in vivo efficacy.

Haloperidol-Induced Catalepsy Grid Test

A haloperidol-induced catalepsy model in mice was used to evaluate the effects of AAV vector-mediated expression of NPY and its receptors on the cataleptic state. This model employs administrating haloperidol known to antagonize dopamine D2 receptors and reduce striatal dopamine content. This leads to resultant block of dopaminergic transmission and abnormal downstream firing within the basal ganglia circuits, which manifests as symptoms of rigidity and catalepsy, mimicking the motor symptoms observed in Parkinson's disease.

Figure 9A:
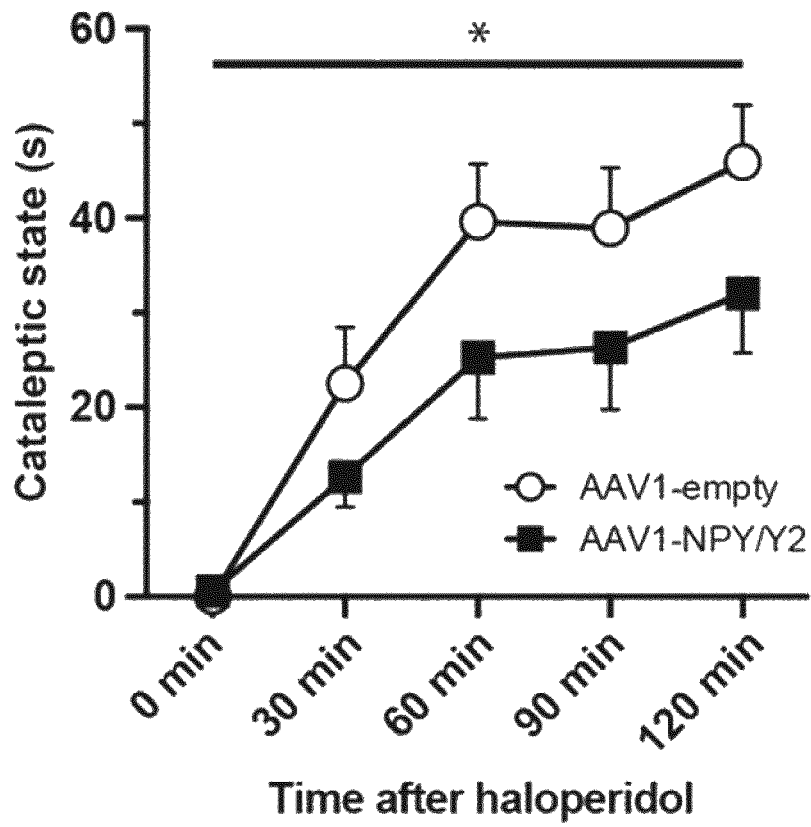
FIG. 9 illustrates effects of bilateral intrastriatal AAV1-NPY/Y2 or AAV-empty (control) vector injections in mice, in the haloperidol-induced catalepsy of Parkinsonian symptoms. A) Treatment with AAV1-NPY/Y2 vector induced a significant reduction in time spent in cataleptic state as compared to AAV1-empty. Data are presented as mean values±s.e.m and analyzed using two-way repeated-measures ANOVA. *P<0.05 indicates an overall significant treatment effect between AAV1-empty and AAV1-NPY/Y2 vector treatments. B) Treatment with AAV1-NPY/Y2 vector induced a significant reduction in mean time spent in cataleptic state observed in 15-minutes intervals, as compared to AAV1-empty. Data are presented as mean values±s.e.m and analyzed using two-way Student's t-test. *P<0.05.
Figure 9B:
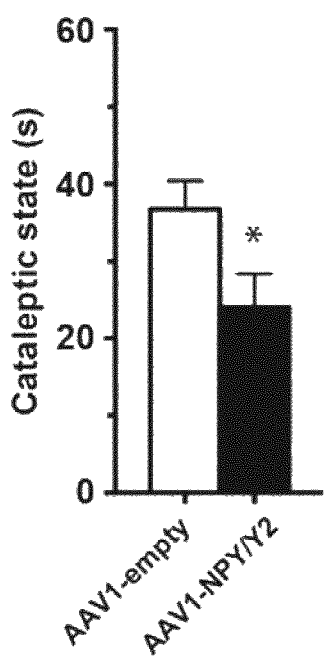

As can be seen in FIG. 9A, AAV1-NPY/Y2 vector injections in mice induced a significant reduction in time spent in cataleptic state as compared to AAV1-empty. Furthermore, FIG. 9B illustrates that treatment with the AAV1-NPY/Y2 vector also induced a significant reduction in mean time spent in cataleptic state observed in 15-minutes intervals, as compared to AAV1-empty.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Experimental

The following examples are mere examples and should by no mean be interpreted to limit the scope of the invention. Rather, the invention is limited only by the accompanying claims.

Vectors

Human NPY (NM_000905.3) and NPY2R (NM_000910.2) open reading frames (ORFs) as well as the internal ribosome entry site (IRES sequence, A7 version) were cloned into an AAV expression plasmid under the control of a 0.9 kb hybrid cytomegalovirus enhancer/chicken β-actin (CAG) promoter and containing a woodchuck hepatitis post-transcriptional regulatory element (WPRE) and bovine growth hormone polyadenylation (bGH) signal flanked by AAV2 inverted terminal repeats. The resulting vectors are summarized schematically in FIGS. 1A and 1B.

Packaging of AAV Vector Genomes into AAV Particles

The vector DNA is transfected into permissive eukaryotic cells (such as human 293 cells) in the presence of a complementing AAV genome (such as pAV2 (ATCC)) or recombinant AAV-plasmid. The cells are cultivated for 2 to 4 days (in LB plus ampicillin at 37° C.) after which the viral particles are released through multiple freeze/thaw cycles after which the adenovirus helper virus is inactivated through heating to 60° C. The resulting cell lysate contains AAV particles having the AAV vector packaged in AAV particles. Using the two vectors described above, and AAV1, 2, 8 helper virus, 6 different AAV particles can be obtained. All produced vectors consists of the above mentioned AAV plasmid constructs with the ITR from AAV serotype 2, packaged in so-called pseudo-typed AAV particles, meaning that they are coated with capsid proteins from AAV serotypes 1, 2, and 8.

AAV Vector Injections into the Rat Hippocampus

The AAV vectors were anaesthetized and injected unilaterally into the dorsal hippocampus (Coordinate set 1: Anterior-Posterior −3.3 mm, Medial-Lateral 1.8 mm, Dorsal-Ventral −2.6 mm from dura or Coordinate set 2: Anterior-Posterior −4.0 mm, Medial-Lateral −2.1 mm, Dorsal-Ventral −4.3 mm from skull surface) or bilaterally into the dorsoventral hippocampus (anterior-posterior −3.3 mm, medial-lateral +/−1.8 mm, dorsal-ventral −2.6 mm, AP−4.8 mm, ML±5.2 mm, DV−6.4 and −3.8 mm) in adult male Wistar rats. Reference points were bregma for the anterior-posterior axis, midline for the medial-lateral axis. A volume of 1 or 3 µl viral vector suspension ($1.1 \times 10^{12}$ genomic particles/ml) per hemisphere was infused.

Kainate-Induced Seizures in Rats

Three weeks after AAV vector injections rats were injected subcutaneously with kainate (KA; 10 mg/kg; diluted in 0.9% isotonic saline; pH 7.4) and placed in individual Plexiglas boxes (30×19×29 cm) and video-recorded for 2 h. Subsequently, an observer unaware of the treatment condition, rated latency to first motor seizure and status epilepticus, time spent in motor seizures, as well as number of seizures. Motor seizures were defined as clonic movement of the fore- and/or hindlimbs for at least 15 s duration.

Euthanization and Tissue Collection from Rats

Three hours after KA injection animals were deeply anaesthetized and decapitated. The brains were quickly collected and snap frozen on dry ice, and subsequently stored at -80° C. until further processing.

Assessment of AAV Vector-Mediated Transgene Expression in Rats

The expression levels after AAV vector treatments were compared to expression levels in corresponding treatment naïve control rats. The expression levels and distribution patterns of the two transgenes NPY and NPY2R were assessed using ddPCR, immunohistochemical and autoradiographic assays on cells or hippocampal brain slices from the treated animals.

Droplet digital PCR (ddPCR) assay: RNA was isolated from Human Embryonic Kidney 293 cells transfected with the AAV-NPY/Y2 or AAV-Y2/NPY vectors. cDNA was synthsised using iScript Advanced cDNASynthesis kit for RT-qPCR (Bio-Rad). Primers and probe assays (Integrated DNA Technologies) for ddPCR were designed using Integrated DNA Technologies RealTime qPCR Assay design tool: NPY (forward: CTCATCACCAGGCAGAGATATG (SEQ ID NO: 11); reverse: ACCACATTGCAGGGTCTTC (SEQ ID NO: 12)), NPY2R (forward: CTGGACCTGAAGGAGTACAAAC (SEQ ID NO: 13); reverse: GTTCATCCAGCCATAGAGAAGG (SEQ ID NO: 14)). A duplex ddPCR assay measuring FAM-labelled NPY target sequence and HEX-labelled NPY2R target sequence was carried out using the Bio-Rad QX200 platform. 20 µl reactions comprising of 1× ddPCR Supermix for Probes (no dUTP) (Bio-Rad), NPY primers/FAM probe (900 nM/250 nM), NPY2R primers/HEX probe (900 nM/250 nM) and 2 µl of cDNA diluted 1:5000 were used for droplet generation and PCR. Standard cycling conditions for Droplet Digital PCR (BioRad C1000 Touch thermal cycler) with annealing/extension temperature of 60° C. were used. Samples were analysed on the QX200 droplet reader (BioRad) using QuantaSoft™ software (BioRad).

NPY immunohistochemical assay: Incubation with rabbit anti-NPY antibody (1:500/1:10,000; Sigma-Aldrich) followed by incubation with Cy3-conjugated Donkey anti-rabbit antibody (1:200, Jackson Immunoresearch, USA) or biotinylated donkey anti-rabbit secondary antibody and 3,3-diaminobenzidine (DAB) was used for visualization of NPY expression in the hippocampal slices. Digitized images were obtained using an Olympus BX61 microscope and CellSens software. NPY levels were rated in the dorsal hippocampal CA1 (pyramidal layer and strata oriens and radiatum) after qualitative evaluation and given values corresponding to the NPY-positive signal: 1 (NPY levels corresponding to endogenous levels), 2 (low NPY expression above the endogenous level), 3 (moderate NPY expression above the endogenous level), and 4 (high NPY expression above the endogenous level). Data are presented as mean values±s.e.m and analyzed using Mann-Whitney U test. *$P<0.05$ as compared to untreated naïve control animals.

NPY Y2 receptor binding autoradiography assay: The hippocampal slices were incubated with 0.1 nM [$^{125}$I][Tyr36]monoiodo-PYY (4000 Ci/mmol; #IM259; Amersham Biosciences) together with 10 nM Leu31,Pro34-neuropeptide Y (Y1/Y4/Y5 preferring agonist; #H-3306, Bachem AG, Switzerland) to visualize Y2 binding. 1 microM non-labeled NPY (human/rat synthetic, Schafer-N, Denmark) was added to visualize non-specific binding. Subsequently, the slices were exposed to 125I-sensitive Kodak Biomax MS films (Amersham Biosciences) and developed. Y2 receptor binding was rated in the dorsal hippocampal CA1 (pyramidal layer and strata oriens and radiatum) after qualitative evaluation and given values corresponding to the Y2 receptor signal: 1 (Y2 receptor expression corresponding to endogenous levels), 2 (low Y2 receptor expression above the endogenous level), 3 (moderate Y2 receptor expression above the endogenous level), and 4 (high Y2 receptor expression above the endogenous level). Data are presented as mean values±s.e.m and analyzed using Mann-Whitney U test. *$P<0.05$ as compared to untreated naïve control animals.

NPY Y2 functional receptor binding autoradiography assay: The hippocampal slices were incubated with 40 pM [$^{35}$S]-GTPγS (1250 Ci/mmol; NEG030H250UC; PerkinElmer, DK), 1 µM NPY (Schafer-N, Copenhagen, DK), 1 µM Y1 receptor antagonist BIBP3226 (#E3620, Bachem AG, Switzerland), and 10 µM Y5 receptor antagonist L-152,804 (#1382, Tocris Cookson, UK) for visualization of Y2 receptor functional binding. To confirm Y2 receptor binding, 1 µM Y2 receptor antagonist BIIE0246 (#1700, Tocris Cookson, UK) was added to NPY together with BIBP3226 and L-152,804. Non-specific binding is determined by incubation in buffer B with 40 pM [$^{35}$S]-GTPγS and 10 microM non-labelled GTPγS (#89378; Sigma-Aldrich). Subsequently, the slices were exposed to Kodak BioMax MR films and developed. Y2 receptor functional binding was rated in dorsal hippocampal CA1 (pyramidal layer and strata oriens and radiatum) using the ImageJ software (National Institute of Health, USA). Data are presented as mean values±s.e.m and analyzed using two-tailed Student's t-test. *P<0.05, ***P<0.001 as compared to untreated naïve control animals.

AAV Vector Injections into the Mouse Striatum

The mice were anaesthetized and injected with viral vector ($1.1 \times 10^{12}$ genomic particles/ml) at three sites with the following coordinates relative to bregma: Anterior-Posterior: +0.85 mm; Medial-Lateral: ±1.85 mm; Dorsal-Ventral: −3.00 mm (1 µl), −3.4 mm (0.5 µl), −3.85 mm (1 µl) using cranium externum as reference point).

Haloperidol-Induced Catalepsy Grid Test in Mice

This commonly used pharmacological model of symptoms in Parkinson's disease employs administration of haloperidol known to antagonize dopamine D2 receptors and reduce striatal dopamine content (Duty and Jenner, 2011). This leads to resultant block of dopaminergic transmission and abnormal downstream firing within the basal ganglia circuits, which manifests as symptoms of rigidity and catalepsy, mimicking the motor symptoms observed in Parkinson's disease.

The mice were injected with haloperidol (1.0 mg/kg, i.p.) and tested by placing the mouse on a metal grid for a period of 60 seconds and note immobilization time. This was done for a 60 seconds observation periods every 30 min during the 2-hour observation period, after the haloperidol injection, by an observer unaware of the treatment conditions.

REFERENCE LIST

Adewale A S, et al., 2005. Neuropeptide Y induced modulation of dopamine synthesis in the striatum. Regul Pept 129:73-78.

Adewale A S, et al., 2007. Neuropeptide Y-induced enhancement of the evoked release of newly synthesized dopamine in rat striatum: mediation by Y2 receptors. Neuropharmacology 52:1396-1402

Altschul, S. F., Madden, T. L., Schäffer A. A., Zhang, J., Zhang, Z., Miller, W., Lipman, D. J., 1997. Gapped BLAST and PSI-BLAST: a new generation of protein database search programs. Nucleic Acids Res., 25,3389-3402.

Bartus R T, Weinberg M S, Samulski R J, 2014. Parkinson's disease gene therapy: success by design meets failure by efficacy. Mol Ther 22:487-497.

Benmaamar, R., Pham-Le, B. T., Marescaux, C., Pedrazzini, T., Depaulis, A., 2003. Induced down-regulation of neuropeptide Y-Y1 receptors delays initiation of kindling. Eur. J. Neurosci. 18,768-774.

Benmaamar, R., Richichi, C., Gobbi, M., Daniels, A. J., Beck-Sickinger, A. G., Vezzani, A., 2005. Neuropeptide Y Y5 receptors inhibit kindling acquisition in rats. Regul. Pept. 125,79-83.

Bochkov, Y. A., Palmenberg, A. C., 2006. Translational efficiency of EMCV IRES in bicistronic vectors is dependent upon IRES sequence and gene location. Biotechniques 41:283-290.

Cannizzaro C, et al., 2003. Increased neuropeptide YmRNA expression in striatum in Parkinson's disease. Brain Res Mol Bain Res 110:169-176.Decressac M, et al., 2011. Exogenous neuropeptide Y promotes in vivo hippocampal neurogenesis. Hippocampus 21:233-238.

Decressac M, et al., 2012. Neuroprotection by neuropeptide Y in cell and animal models of Parkinson's disease. Neurobiol Aging 33:2125-37.

Devereux, J., Haeberli, P., Smithies, O., 1984. A comprehensive set of sequence analysis programs for the VAX. Nucleic Acids Res., 12, 387-395.

Duty, S., Jenner, P., 2011. Animal models of Parkinson's disease: a source of novel treatments and clues to the cause of the disease. British Journal of Pharmacology, 165,1357-1391.

Foti, S., Haberman, R. P., Samulski, R. J., McCown, T. J., 2007. Adeno-associated virusmediated expression and constitutive secretion of NPY or NPY13-36 suppresses seizure activity in vivo. Gene Ther. 14,1534-1536.

Goodwin, E. C., Rottman, F. M., 1992. The 3'-flanking sequence of the bovine growth hormone gene contains novel elements required for efficient and accurate polyadenylation. J. Biochem. 23:16330-16334.

Gøtzsche C R, Nikitidou L, Sørensen A T, Olesen M V, Sørensen G, Christiansen S H, Ängehagen M, Woldbye D P, Kokaia M. Combined gene overexpression of neuropeptide Y and its receptor Y5 in the hippocampus suppresses seizures. Neurobiol Dis. 2012, 45:288-96.

Kerkerian-Le Goff, et al., 1986. Striatal neuropeptide Y neurones are under the influence of the nigrostriatal dopaminergic pathway: immunohistochemical evidence. Neurosci Lett 66:106-112.Ledri M, Sørensen A T, Madsen M G, Christiansen S H, Ledri L N, Cifra A, Bengzon J, Lindberg E, Pinborg L H, Jespersen B, Gøtzsche C R, Woldbye D P, Andersson M, Kokaia M. Differential Effect of Neuropeptides on Excitatory Synaptic Transmission in Human Epileptic Hippocampus. J Neurosci. 2015, 35:9622-31.

Ledri, L. N., Melin, E., Christiansen, S. H., Gøtzsche, C. R., Cifra, A., Woldbye, D. P., Kokaia, M, 2016. Translational approach for gene therapy in epilepsy: Model system and unilateral overexpression of neuropeptide Y and Y2 receptors. Neurobiol.Dis. 86, 52-61.

McCown T J, 2011. Adeno-associated virus (AAV) vectors in the CNS. Curr Gene Ther 2011, 11:181-188.

Myers E. W., Miller, W., 1988. Optimal alignments in linear space. Comput. Appl. Biosci., 4, 11-17.

Olesen, M. V., Christianse, S. H., Gøtzsche, C. R., Nikitidou, L., Kokaia, M., Woldbye, D. P. D., 2012. Neuropeptide Y Y1 receptor hippocampal overexpression via viral vectors is associated with modest anxiolytic-like and proconvulsant effects in mice. J Neurosci Res, 90, 498-507.

Patrylo P R, van den Pol A N, Spencer D D, Williamson A. NPY inhibits glutamatergic excitation in the epileptic human dentate gyms. J Neurophysiol. 1999, 82:478-83.

Pearson, W. R., 1990. Rapid and sensitive sequence comparison with FASTP and FASTA. Methods Enzymol., 183, 63-98.

Rees, S., J. Coote, J. Stables, S. Goodson, S. Harris, and M. G. Lee, 1996. Bicistronic vector for the creation of stable mammalian cell lines that predisposes all antibiotic-resistant cells to express recombinant protein. BioTechniques 20:102-110.

Rose J B, et al., 2009. Neuropeptide Y fragments derived from neprilysin processing are neuroprotective in a transgenic model of Alzheimer's disease. J Neurosci, 29:1115-1125.

Salin P, et al., 1990. Expression of neuropeptide Y immunoreactivity in the rat nucleus accumbens is under the influence of the dopaminergic mesencephalic pathway. Exp Brain Res, 81:363-371.

Shaw J L, et al., 2003. Functional autoradiography of neuropeptide Y Y1 and Y2 receptor subtypes in rat brain using agonist stimulated [35S]GTPgammaS binding. J Chem Neuroanat 26:179-193.Watakabe, A, Ohtsuka, M, Kinoshita, M, Takaji, M, Isa, K, Mizukami, H, Ozawa, K, et al. (2015). Comparative analyses of adeno-associated viral vector serotypes 1, 2, 5, 8 and 9 in marmoset, mouse and macaque cerebral cortex. Neurosci Res 93:144-157.

Woldbye D P, Larsen P J, Mikkelsen J D, Klemp K, Madsen T M, Bolwig T G. Powerful inhibition of kainic acid seizures by neuropeptide Y via Y5-like receptors. Nat Med. 1997, 3:761-4.

Woldbye, D. P., Nanobashvili, A., Sørensen, A. T., Husum, H., Bolwig, T. G., Sørensen, G., et al., 2005. Differential suppression of seizures via Y2 and Y5 neuropeptide Y receptors. Neurobiol. Dis. 20, 760-772.

Woldbye, D. P., Ängehagen, M., Gøtzsche, C. R., Elbrønd-Bek, H., Sørensen, A. T., Christiansen, S. H., et al., 2010. Adeno-associated viral vector-induced overexpression of neuropeptide Y Y2 receptors in the hippocampus suppresses seizures. Brain 133, 2778-2788.

---

The invention claimed is:

1. A recombinant adeno-associated viral (rAAV) vector comprising the following sequences in order:

```
5'-ITR, CAG, NPY, IRES, NPY2R, WPRE, BGHpA, and
ITR-3'
``` wherein said sequences are operably linked on said rAAV vector and, wherein said rAAV vector comprises at least 95% sequence identity to SEQ ID NO: 9.

2. The rAAV vector of claim 1, wherein said rAAV vector has been codon optimized for expression in humans.

3. An adeno-associated virus 1 (AAV 1) particle, comprising a recombinant adeno-associated viral (rAAV) vector, wherein said rAAV vector comprises the following sequences in order:

```
5'-ITR, CAG, NPY, IRES, NPY2R, WPRE, BGHpA, and
ITR-3'
``` wherein said sequences are operably linked on said rAAV vector, wherein said rAAV vector comprises at least 95% sequence identity to SEQ ID NO: 9; and
wherein said rAAV vector is encapsulated by adeno-associated virus (AAV) capsid proteins.

4. The AAV 1 particle of claim 3, wherein the sequence of said rAAV vector has been codon optimized for expression in humans.

* * * * *

UNITED STATES PATENT AND TRADEMARK OFFICE
CERTIFICATE OF CORRECTION

PATENT NO. : 11,072,804 B2
APPLICATION NO. : 16/070443
DATED : July 27, 2021
INVENTOR(S) : Merab Kokaia It is certified that error appears in the above-identified patent and that said Letters Patent is hereby corrected as shown below:

On the Title Page

In Column 2, item (57), Abstract, Line 2, delete "(r AAV)" and insert -- (rAAV) --.

In the Specification

In Column 2, Line 33, delete "donot" and insert -- do not --.

In Column 2, Line 48, delete "sequences (ITR)," and insert -- (ITR) sequences, --.

In Column 3, Line 48, delete "student′s" and insert -- Student′s --.

In Column 4, Line 1, delete "FIG." and insert -- FIGS. --.

In Column 6, Line 7, delete "anti-epileptic" and insert -- antiepileptic --.

In Column 6, Lines 24-25, delete "anti-epileptic" and insert -- antiepileptic --.

In Column 6, Line 26, delete "anti-epileptic" and insert -- antiepileptic --.

In Column 7, Line 4, delete "c.f" and insert -- c.f. --.

In Column 9, Line 32, delete "signal (BGHpA)," and insert -- (BGHpA) signal, --.

In Column 12, Lines 18-19, delete "signal (BGHpA)," and insert -- (BGHpA) signal, --.

In Column 17, Line 50(approx.), delete "sequences (ITR)," and insert -- (ITR) sequences, --.

In Column 18, Line 17(approx.), delete "the a" and insert -- the --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,072,804 B2

In Column 19, Line 27, delete "anti epileptic" and insert -- antiepileptic --.

In Column 22, Line 66, delete "heterologus" and insert -- heterologous --.

In Column 26, Line 65, delete "(bGH)" and insert -- (BGHpA) --.

In Column 27, Line 60, delete "synthsised" and insert -- synthesized --.

In Column 28, Line 66, delete "BioMax" and insert -- Biomax --.

In Column 29, Line 12(approx.), delete "point)." and insert -- point. --.

In Column 29, Line 40(approx.), delete "1402" and insert -- 1402. --.

In Column 30, Line 46, delete "gyms." and insert -- gyrus. --.

In the Claims

In Column 49, Line 14, Claim 3, delete "(AAV 1)" and insert -- (AAV1) --.

In Column 49, Line 28, Claim 4, delete "AAV 1" and insert -- AAV1 --.

SEQUENCE LISTING

<160> NUMBER OF SEQ ID NOS: 16

<210> SEQ ID NO 1
<211> LENGTH: 294
<212> TYPE: DNA
<213> ORGANISM: Homo sapiens

<400> SEQUENCE: 1

```
atgctaggta acaagcgact ggggctgtcc ggactgaccc tcgccctgtc cctgctcgtg    60
tgcctgggtg cgctggccga ggcgtacccc tccaagccga caacccggg cgaggacgca   120
ccagcggagg acatggccag atactactcg gcgctgcgac actacatcaa cctcatcacc   180
aggcagagat atggaaaacg atccagccca gagacactga tttcagacct cttgatgaga   240
gaaagcacag aaaatgttcc cagaactcgg cttgaagacc ctgcaatgtg gtga         294
```

<210> SEQ ID NO 2
<211> LENGTH: 1146
<212> TYPE: DNA
<213> ORGANISM: Homo sapiens

<400> SEQUENCE: 2

```
atgggtccaa taggtgcaga ggctgatgag aaccagacag tggaagaaat gaaggtggaa    60
caatacgggc cacaaacaac tcctagaggt gaactggtcc ctgaccctga gccagagctt   120
atagatagta ccaagctgat tgaggtacaa gttgttctca tattggccta ctgctccatc   180
atcttgcttg gggtaattgg caactccttg gtgatccatg tggtgatcaa attcaagagc   240
atgcgcacag taaccaactt tttcattgcc aatctggctg tggcagatct tttggtgaac   300
actctgtgtc taccgttcac tcttacctat accttaatgg gggagtggaa aatgggtcct   360
gtcctgtgcc acctggtgcc ctatgcccag ggcctggcag tacaagtatc cacaatcacc   420
ttgacagtaa ttgccctgga ccggcacagg tgcatcgtct accacctaga gagcaagatc   480
tccaagcgaa tcagcttcct gattattggc ttggcctggg gcatcagtgc cctgctggca   540
agtcccctgg ccatcttccg ggagtattcg ctgattgaga tcattccgga ctttgagatt   600
gtggcctgta ctgaaaagtg gcctggcgag gagaagagca tctatggcac tgtctatagt   660
cttctcttcct tgttgatctt gtatgttttg cctctgggca ttatatcatt ttcctacact   720
cgcatttgga gtaaattgaa gaaccatgtc agtcctggag ctgcaaatga ccactaccat   780
cagcgaaggc aaaaaaccac caaatgctg gtgtgtgtgg tggtggtgtt tgcggtcagc   840
tggctgcctc tccatgcctt ccagcttgcc gttgacattg acagccaggt cctggacctg   900
aaggagtaca aactcatctt cacagtgttc cacattatcg ccatgtgctc cacttttgcc   960
aatccccttc tctatggctg gatgaacagc aactacagaa aggctttcct ctcggccttc  1020
cgctgtgagc agcggttgga tgccattcac tctgaggtgt ccgtgacatt caaggctaaa  1080
aagaacctgg aggtcagaaa gaacagtggc cccaatgact ctttcacaga ggctaccaat  1140
gtctaa                                                             1146
```

<210> SEQ ID NO 3
<211> LENGTH: 582
<212> TYPE: DNA
<213> ORGANISM: Artificial Sequence
<220> FEATURE:
<223> OTHER INFORMATION: A7 EMCV IRES

<400> SEQUENCE: 3

```
cgcccctctc cctcccccccc ccctaacgtt actggccgaa gccgcttgga ataaggccgg    60
tgtgcgtttg tctatatgtt attttccacc atattgccgt cttttggcaa tgtgagggcc   120
cggaaacctg gccctgtctt cttgacgagc attcctaggg gtctttcccc tctcgccaaa   180
ggaatgcaag gtctgttgaa tgtcgtgaag gaagcagttc ctctggaagc ttcttgaaga   240
caaacaacgt ctgtagcgac cctttgcagg cagcggaacc ccccacctgg cgacaggtgc   300
ctctgcggcc aaaagccacg tgtataagat acacctgcaa aggcggcaca accccagtgc   360
cacgttgtga gttggatagt tgtggaaaga gtcaaatggc tctcctcaag cgtattcaac   420
aaggggctga aggatgccca aaggtaccc cattgtatgg gatctgatct ggggcctcgg   480
tgcacatgct ttcatgtgt ttagtcgagg ttaaaaaaac gtctaggccc cccgaaccac   540
ggggacgtgg ttttcctttg aaaaacacga tgataagtcg ac                      582
```

<210> SEQ ID NO 4
<211> LENGTH: 936
<212> TYPE: DNA
<213> ORGANISM: Artificial Sequence
<220> FEATURE:
<223> OTHER INFORMATION: CAG Promotor

<400> SEQUENCE: 4

```
cattgacgtc aataatgacg tatgttccca tagtaacgcc aatagggact ttccattgac    60
gtcaatgggt ggagtattta cggtaaactg cccacttggc agtacatcaa gtgtatcata   120
tgccaagtac gccccctatt gacgtcaatg acggtaaatg gcccgcctgg cattatgccc   180
agtacatgac cttatgggac tttcctactt ggcagtacat ctacgtatta gtcatcgcta   240
ttaccatggt cgaggtgagc cccacgttct gcttcactct ccccatctcc ccccctccc   300
cacccccaat tttgtattta tttattttt aattattttg tgcagcgatg gggcggggg    360
gggggggggg gcgcgcgcca ggcggggcgg ggcggggcga gggcggggc ggggcgaggc    420
ggagaggtgc ggcggcagcc aatcagagcg gcgcgctccg aaagtttcct tttatggcga   480
ggcggcggcg gcggcggccc tataaaaagc gaagcgcgcg gcgggcggga gtcgctgcgc   540
gctgccttcg ccccgtgccc cgctccgccg ccgcctcgcg ccgcccgccc ggctctgac   600
tgaccgcgtt actcccacag gtgagcgggc gggacggcc ttctcctccg ggctgtaatt   660
agcgcttggt ttaatgacgg cttgtttctt ttctgtggct gcgtgaaagc cttgaggggc   720
tccgggaggg ccctttgtgc gggggagcg gctcggggct gtccgcgggg gacggctgc    780
cttcgggggg gacggggcag ggcggggttc ggcttctggc gtgtgaccgg cggctctaga   840
gcctctgcta accatgttca tgccttcttc ttttccctac agctcctggg caacgtgctg   900
gttattgtgc tgtctcatca ttttggcaaa gaattg                              936
```

<210> SEQ ID NO 5
<211> LENGTH: 593
<212> TYPE: DNA
<213> ORGANISM: Artificial Sequence
<220> FEATURE:

```
<223> OTHER INFORMATION: WPRE

<400> SEQUENCE: 5
atcgataatc aacctctgga ttacaaaatt tgtgaaagat tgactggtat tcttaactat      60
gttgctcctt ttacgctatg tggatacgct gctttaatgc cttgtatca tgctattgct     120 tcccgtatgg ctttcatttt ctcctccttg tataaatcct ggttgctgtc tctttatgag    180
gagttgtggc ccgttgtcag gcaacgtggc gtggtgtgca ctgtgtttgc tgacgcaacc    240
cccactggtt ggggcattgc caccacctgt cagctccttt ccgggacttt cgctttcccc    300
ctccctattg ccacggcgga actcatcgcc gcctgcttg cccgctgctg acagggggct     360
cggctgttgg gcactgacaa ttccgtggtg ttgtcgggga atcatcgtc ctttccttgg     420 ctgctcgcct gtgttgccac ctggattctg cgcgggacgt ccttctgcta cgtcccttcg    480
gccctcaatc cagcggacct tccttcccgc ggcctgctgc cggctctgcg gcctcttccg    540
cgtcttcgcc ttcgccctca gacgagtcgg atctcccttt gggccgcctc ccc           593

<210> SEQ ID NO 6
<211> LENGTH: 269
<212> TYPE: DNA
<213> ORGANISM: Artificial Sequence
<220> FEATURE:
<223> OTHER INFORMATION: bGH-polyA

<400> SEQUENCE: 6
cgctgatcag cctcgactgt gccttctagt tgccagccat ctgttgtttg cccctccccc     60
gtgccttcct tgaccctgga aggtgccact cccactgtcc tttcctaata aaatgaggaa    120
attgcatcgc attgtctgag taggtgtcat tctattctgg ggggtggggt ggggcaggac    180
agcaaggggg aggattggga agacaatagc aggcatgctg gggatgcggt gggctctatg    240
gcttctgagg cggaaagaac cagctgggg                                     269

<210> SEQ ID NO 7
<211> LENGTH: 183
<212> TYPE: DNA
<213> ORGANISM: Artificial Sequence
<220> FEATURE:
<223> OTHER INFORMATION: 5' end ITR

<400> SEQUENCE: 7
tagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagccatgc    180
tct                                                                 183

<210> SEQ ID NO 8
<211> LENGTH: 183
<212> TYPE: DNA
<213> ORGANISM: Artificial Sequence
<220> FEATURE:
<223> OTHER INFORMATION: 3' end ITR

<400> SEQUENCE: 8
agcatggcta cgtagataag tagcatggcg ggttaatcat taactacaag gaaccccctag    60 tgatggagtt ggccactccc tctctgcgcg ctcgctcgct cactgaggcc gggcgaccaa    120
aggtcgcccg acgcccgggc tttgcccggg cggcctcagt gagcgagcga gcgcgcagag    180
ctt                                                                 183
```

<210> SEQ ID NO 9
<211> LENGTH: 4288
<212> TYPE: DNA
<213> ORGANISM: Artificial Sequence
<220> FEATURE:
<223> OTHER INFORMATION: ITR-CAG-NPY-IRES-NPY2R-WPRE-BGHpA-ITR

<400> SEQUENCE: 9

```
tagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtagccatgc     180
tctaggtacc attgacgtca ataatgacgt atgttcccat agtaacgcca atagggactt     240
tccattgacg tcaatgggtg gagtatttac ggtaaactgc ccacttggca gtacatcaag     300
tgtatcatat gccaagtacg ccccctattg acgtcaatga cggtaaatgg cccgcctggc     360
attatgccca gtacatgacc ttatgggact ttcctacttg gcagtacatc tacgtattag     420
tcatcgctat taccatggtc gaggtgagcc ccacgttctg cttcactctc cccatctccc     480
cccctcccc accccaatt ttgtatttat ttattttta attattttgt gcagcgatgg     540
ggcgggggg ggggggggg cgcgcgccag gcggggcggg gcggggcgag gggcggggcg     600
gggcgaggcg gagaggtgcg gcggcagcca atcagagcgg cgcgctccga aagtttcctt     660
ttatggcgag gcggcggcgg cggcggccct ataaaaagcg aagcgcgcgg cgggcgggag     720
tcgctgcgcg ctgccttcgc cccgtgcccc gctccgccgc cgcctcgcgc cgcccgcccc     780
ggctctgact gaccgcgtta ctcccacagg tgagcgggcg ggacggccct tctcctccgg     840
gctgtaatta gcgcttggtt taatgacggc ttgtttcttt tctgtggctg cgtgaaagcc     900
ttgagggct ccgggagggc cctttgtgcg ggggagcgg ctcggggctg tccgcggggg     960
gacggctgcc ttcgggggg acggggcagg gcggggttcg gcttctgcg tgtgaccggc    1020
ggctctagag cctctgctaa ccatgttcat gccttcttct ttttcctaca gctcctgggc    1080
aacgtgctgg ttattgtgct gtctcatcat tttggcaaag aattggatcc actcgagatg    1140
ctaggtaaca agcgactggg gctgtccgga ctgaccctcg ccctgtccct gctcgtgtgc    1200
ctgggtgcgc tggccgaggc gtaccccctcc aagccggaca acccgggcga ggacgcacca    1260
gcggaggaca tggccagata ctactcggcg ctgcgacact acatcaacct catcaccagg    1320
cagagatatg gaaaacgatc cagcccagag acactgattt cagacctctt gatgagagaa    1380
agcacagaaa atgttcccag aactcggctt gaagaccctg caatgtggtg acaattgcgc    1440
ccctctccct cccccccccc taacgttact ggccgaagcc gcttggaata aggccggtgt    1500
gcgtttgtct atatgttatt ttccaccata ttgccgtctt ttggcaatgt gagggcccgg    1560
aaacctggcc ctgtcttctt gacgagcatt cctagggtc tttccctct cgccaaagga    1620
atgcaaggtc tgttgaatgt cgtgaaggaa gcagttcctc tggaagcttc ttgaagacaa    1680
acaacgtctg tagcgaccct ttgcaggcag cggaaccccc cacctggcga caggtgcctc    1740
tgcggccaaa agccacgtgt ataagataca cctgcaaagg cggcacaacc ccagtgccac    1800
gttgtgagtt ggatagttgt ggaaagagtc aaatggctct cctcaagcgt attcaacaag    1860
gggctgaagg atgcccagaa ggtaccccat tgtatggat ctgatctggg gcctcggtgc    1920
acatgcttta catgtgttta gtcgaggtta aaaaaacgtc taggcccccc gaaccacggg    1980
gacgtggttt ccttttgaaa aacacgatga taagtcgaca ctagcatggg tccaataggt    2040
```

```
gcagaggctg atgagaacca gacagtggaa gaaatgaagg tggaacaata cgggccacaa    2100
acaactccta gaggtgaact ggtccctgac cctgagccag agcttataga tagtaccaag    2160
ctgattgagg tacaagttgt tctcatattg gcctactgct ccatcatctt gcttggggta    2220
attggcaact ccttggtgat ccatgtggtg atcaaattca agagcatgcg cacagtaacc    2280 aacttttca ttgccaatct ggctgtggca gatcttttgg tgaacactct gtgtctaccg     2340
ttcactctta cctataccttaatggggag tggaaaatgg gtcctgtcct gtgccacctg      2400
gtgccctatg cccagggcct ggcagtacaa gtatccacaa tcaccttgac agtaattgcc    2460
ctggaccggc acaggtgcat cgtctaccac ctagagagca agatctccaa gcgaatcagc    2520
ttcctgatta ttggcttggc ctggggcatc agtgccctgc tggcaagtcc cctggccatc    2580
ttccgggagt attcgctgat tgagatcatt ccggactttg agattgtggc ctgtactgaa    2640
aagtggcctg gcgaggagaa gagcatctat ggcactgtct atagtctttc ttccttgttg    2700
atcttgtatg ttttgcctct gggcattata tcattttcct acactcgcat ttggagtaaa    2760
ttgaagaacc atgtcagtcc tggagctgca aatgaccact accatcagcg aaggcaaaaa    2820
accaccaaaa tgctggtgtg tgtggtggtg gtgtttgcgg tcagctggct gcctctccat    2880
gccttccagc ttgccgttga cattgacagc caggtcctgg acctgaagga gtacaaactc    2940
atcttcacag tgttccacat tatcgccatg tgctccactt ttgccaatcc ccttctctat    3000
ggctggatga acagcaacta cagaaaggct ttcctctcgg ccttccgctg tgagcagcgg    3060
ttggatgcca ttcactctga ggtgtccgtg acattcaagg ctaaaaagaa cctggaggtc    3120
agaaagaaca gtgcccccaa tgactctttc acagaggcta ccaatgtcta aggatccact    3180
agtccagtgt ggtggaattc gatatcaagc ttatcgataa tcaacctctg gattacaaaa    3240
tttgtgaaag attgactggt attcttaact atgttgctcc ttttacgcta tgtggatacg    3300
ctgctttaat gcctttgtat catgctattg cttcccgtat ggctttcatt ttctcctcct    3360
tgtataaatc ctggttgctg tctctttatg aggagttgtg gcccgttgtc aggcaacgtg    3420
gcgtggtgtg cactgtgttt gctgacgcaa ccccccactgg ttggggcatt gccaccacct    3480
gtcagctcct ttccgggact ttcgctttcc cctcccctat tgccacgcgc gaactcatcg    3540
ccgcctgcct tgcccgctgc tggacagggg ctcggctgtt gggcactgac aattccgtgg    3600
tgttgtcggg gaaatcatcg tccttttcctt ggctgctcgc ctgtgttgcc acctggattc    3660
tgcgcgggac gtccttctgc tacgtccctt cggccctcaa tccagcggac cttccttccc    3720
gcggcctgct gccggctctg cggcctcttc cgcgtcttcg ccttcgccct cagacgagtc    3780
ggatctccct ttgggccgcc tccccgcatc gataccgtcg atcgactcgc tgatcagcct    3840
cgactgtgcc ttctagttgc cagccatctg ttgtttgccc ctcccccgtg ccttccttga    3900
ccctggaagg tgccactccc actgtccttt cctaataaaa tgaggaaatt gcatcgcatt    3960
gtctgagtag gtgtcattct attctggggg gtggggtggg gcaggacagc aaggggggag    4020
attgggaaga caatagcagg catgctgggg atgcggtggg ctctatggct tctgaggcgg    4080
aaagaaccag ctggggctcg actagagcat ggctacgtag ataagtagca tggcgggtta    4140
atcattaact acaaggaacc cctagtgatg gagttggcca ctccctctct gcgcgctcgc    4200
tcgctcactg aggccgggcg accaaaggtc gcccgacgcc cgggctttgc ccgggcggcc    4260
tcagtgagcg agcgagcgcg cagagctt                                       4288

<210> SEQ ID NO 10
<211> LENGTH: 4288
```

<212> TYPE: DNA
<213> ORGANISM: Artificial Sequence
<220> FEATURE:
<223> OTHER INFORMATION: ITR-CAG-NPY2R-IRES-NPY-WPRE-BGHpA-ITR

<400> SEQUENCE: 10

```
tagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtagccatgc     180
tctaggtacc attgacgtca ataatgacgt atgttcccat agtaacgcca atagggactt     240
tccattgacg tcaatgggtg gagtatttac ggtaaactgc ccacttggca gtacatcaag     300
tgtatcatat gccaagtacg ccccctattg acgtcaatga cggtaaatgg cccgcctggc     360
attatgccca gtacatgacc ttatgggact ttcctacttg gcagtacatc tacgtattag     420
tcatcgctat taccatggtc gaggtgagcc ccacgttctg cttcactctc cccatctccc     480
cccctcccc accccccaatt ttgtatttat ttattttta attattttgt gcagcgatgg     540
gggcggggg ggggggggg cgcgcgccag gcggggcggg gcggggcgag gggcggggcg     600
gggcgaggcg gagaggtgcg gcggcagcca atcagagcgg cgcgctccga aagtttcctt     660
ttatggcgag gcggcggcgg cggcggccct ataaaaagcg aagcgcgcgg cgggcgggag     720
tcgctgcgcg ctgccttcgc cccgtgcccc gctccgccgc cgcctcgcgc cgcccgcccc     780
ggctctgact gaccgcgtta ctcccacagg tgagcgggcg ggacggccct tctcctccgg     840
gctgtaatta gcgcttggtt taatgacggc ttgtttctt tctgtggctg cgtgaaagcc     900
ttgaggggct ccgggagggc cctttgtgcg ggggagcgc ctcggggctg tccgcggggg     960
gacggctgcc ttcggggggg acggggcagg gcggggttcg gcttctggcg tgtgaccggc    1020
ggctctagag cctctgctaa ccatgttcat gccttcttct ttttcctaca gctcctgggc    1080
aacgtgctgg ttattgtgct gtctcatcat tttggcaaag aattggatcc actcgacact    1140
agcatgggtc caataggtgc agaggctgat gagaaccaga cagtggaaga atgaaggtg    1200
gaacaatacg ggccacaaac aactcctaga ggtgaactgg tccctgaccc tgagccagag    1260
cttatagata gtaccaagct gattgaggta caagttgttc tcatattggc ctactgctcc    1320
atcatcttgc ttggggtaat tggcaactcc ttggtgatcc atgtggtgat caaattcaag    1380
agcatgcgca cagtaaccaa cttttcatt gccaatctgg ctgtggcaga tcttttggtg    1440
aacactctgt gtctaccgtt cactcttacc tataccttaa tgggggagtg aaaatgggt    1500
cctgtcctgt gccacctggt gcccatgcc cagggcctgg cagtacaagt atccacaatc    1560
accttgacag taattgccct ggaccggcac aggtgcatcg tctaccacct agagagcaag    1620
atctccaagc gaatcagctt cctgattatt ggcttggcct ggggcatcag tgccctgctg    1680
gcaagtcccc tggccatctt ccgggagtat cgctgattg agatcattcc ggactttgag    1740
attgtggcct gtactgaaaa gtggcctggc gaggagaaga gcatctatgg cactgtctat    1800
agtctttctt ccttgttgat cttgtatgtt ttgcctctgg cattatatc attttcctac    1860
actcgcattt ggagtaaatt gaagaaccat gtcagtcctg gagctgcaaa tgaccactac    1920
catcagcgaa ggcaaaaaac caccaaaatg ctggtgtgtg tggtggtggt gtttgcggtc    1980
agctggctgc ctctccatgc cttccagctt gccgttgaca ttgacagcca ggtcctggac    2040
ctgaaggagt acaaactcat cttcacagtg ttccacattta tcgccatgtg ctccactttt    2100
gccaatcccc ttctctatgg ctggatgaac agcaactaca gaaaggcttt cctctcggcc    2160
```

```
ttccgctgtg agcagcggtt ggatgccatt cactctgagg tgtccgtgac attcaaggct    2220
aaaaagaacc tggaggtcag aaagaacagt ggcccccaatg actctttcac agaggctacc   2280
aatgtctaag gatccactag tccagtgtgg tggaattgcg cccctctccc tccccccccc    2340
ctaacgttac tggccgaagc cgcttggaat aaggccggtg tgcgtttgtc tatatgttat    2400
tttccaccat attgccgtct tttggcaatg tgagggcccg gaaacctggc cctgtcttct    2460
tgacgagcat tcctaggggt ctttcccctc tcgccaaagg aatgcaaggt ctgttgaatg    2520
tcgtgaagga agcagttcct ctggaagctt cttgaagaca acaacgtct gtagcgaccc     2580 tttgcaggca gcggaacccc ccacctggcg acaggtgcct ctgcggccaa agccacgtg     2640 tataagatac acctgcaaag gcggcacaac cccagtgcca cgttgtgagt tggatagttg    2700
tggaaagagt caaatggctc tcctcaagcg tattcaacaa ggggctgaag gatgcccaga    2760
aggtacccca ttgtatggga tctgatctgg ggcctcggtg cacatgcttt acatgtgttt    2820
agtcgaggtt aaaaaaacgt ctaggccccc cgaaccacgg ggacgtggtt ttcctttgaa    2880
aaacacgatg ataagtcgag atgctaggta acaagcgact ggggctgtcc ggactgaccc    2940
tcgccctgtc cctgctcgtg tgcctgggtg cgctggccga ggcgtacccc tccaagccgg    3000
acaacccggg cgaggacgca ccagcggagg acatggccag atactactcg cgctgcgac    3060 actacatcaa cctcatcacc aggcagagat atggaaaacg atccagccca gagacactga    3120
tttcagacct cttgatgaga gaaagcacag aaaatgttcc cagaactcgg cttgaagacc    3180
ctgcaatgtg gtgacaattc gatatcaagc ttatcgataa tcaacctctg gattacaaaa    3240
tttgtgaaag attgactggt attcttaact atgttgctcc ttttacgcta tgtggatacg    3300
ctgctttaat gcctttgtat catgctattg cttcccgtat ggctttcatt ttctcctcct    3360
tgtataaatc ctggttgctg tctctttatg aggagttgtg gcccgttgtc aggcaacgtg    3420
gcgtggtgtg cactgtgttt gctgacgcaa ccccccactgg ttggggcatt gccaccacct    3480
gtcagctcct ttccgggact ttcgctttcc ccctccctat gccacggcg gaactcatcg     3540 ccgcctgcct tgcccgctgc tggacagggg ctcggctgtt gggcactgac aattccgtgg    3600
tgttgtcggg gaaatcatcg tccttttcctt ggctgctcgc ctgtgttgcc acctggattc    3660
tgcgcgggac gtccttctgc tacgtccctt cggccctcaa tccagcggac cttccttccc    3720
gcggcctgct gccggctctg cggcctcttc cgcgtcttcg ccttcgccct cagacgagtc    3780
ggatctccct ttgggccgcc tccccgcatc gataccgtcg atcgactcgc tgatcagcct    3840
cgactgtgcc ttctagttgc cagccatctg ttgtttgccc ctcccccgtg ccttccttga    3900
ccctggaagg tgccactccc actgtccttt cctaataaaa tgaggaaatt gcatcgcatt    3960
gtctgagtag tgtcattct attctggggg gtgggtggg gcaggacagc aaggggggagg     4020 attgggaaga caatagcagg catgctgggg atgcggtggg ctctatggct tctgaggcgg    4080
aaagaaccag ctggggctcg actagagcat ggctacgtag ataagtagca tggcgggtta    4140
atcattaact acaaggaacc cctagtgatg gagttggcca ctccctctct gcgcgctcgc    4200
tcgctcactg aggccgggcg accaaaggtc gcccgacgcc cgggctttgc ccgggcggcc    4260
tcagtgagcg agcgagcgcg cagagctt                                      4288
```

<210> SEQ ID NO 11
<211> LENGTH: 22
<212> TYPE: DNA
<213> ORGANISM: Artificial Sequence
<220> FEATURE:
<223> OTHER INFORMATION: NPY forward primer

<400> SEQUENCE: 11
ctcatcacca ggcagagata tg                                              22

<210> SEQ ID NO 12
<211> LENGTH: 19
<212> TYPE: DNA
<213> ORGANISM: Artificial Sequence
<220> FEATURE:
<223> OTHER INFORMATION: NPY reverse primer

<400> SEQUENCE: 12
accacattgc agggtcttc                                                  19

<210> SEQ ID NO 13
<211> LENGTH: 22
<212> TYPE: DNA
<213> ORGANISM: Artificial Sequence
<220> FEATURE:
<223> OTHER INFORMATION: NPY2R forward primer

<400> SEQUENCE: 13
ctggacctga aggagtacaa ac                                              22

<210> SEQ ID NO 14
<211> LENGTH: 22
<212> TYPE: DNA
<213> ORGANISM: Artificial Sequence
<220> FEATURE:
<223> OTHER INFORMATION: NPY2R reverse primer

<400> SEQUENCE: 14
gttcatccag ccatagagaa gg                                              22

<210> SEQ ID NO 15
<211> LENGTH: 97
<212> TYPE: PRT
<213> ORGANISM: Homo sapiens

<400> SEQUENCE: 15

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
            20                  25                  30

Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp

<210> SEQ ID NO 16
<211> LENGTH: 381
<212> TYPE: PRT
<213> ORGANISM: Homo sapiens

<400> SEQUENCE: 16

Met Gly Pro Ile Gly Ala Glu Ala Asp Glu Asn Gln Thr Val Glu Glu
1               5                   10                  15

```
Met Lys Val Glu Gln Tyr Gly Pro Gln Thr Thr Pro Arg Gly Glu Leu
            20                  25                  30

Val Pro Asp Pro Glu Pro Glu Leu Ile Asp Ser Thr Lys Leu Ile Glu
        35                  40                  45

Val Gln Val Val Leu Ile Leu Ala Tyr Cys Ser Ile Ile Leu Leu Gly
    50                  55                  60

Val Ile Gly Asn Ser Leu Val Ile His Val Val Ile Lys Phe Lys Ser
65                  70                  75                  80

Met Arg Thr Val Thr Asn Phe Phe Ile Ala Asn Leu Ala Val Ala Asp
                85                  90                  95

Leu Leu Val Asn Thr Leu Cys Leu Pro Phe Thr Leu Thr Tyr Thr Leu
                100                 105                 110

Met Gly Glu Trp Lys Met Gly Pro Val Leu Cys His Leu Val Pro Tyr
            115                 120                 125

Ala Gln Gly Leu Ala Val Gln Val Ser Thr Ile Thr Leu Thr Val Ile
        130                 135                 140

Ala Leu Asp Arg His Arg Cys Ile Val Tyr His Leu Glu Ser Lys Ile
145                 150                 155                 160

Ser Lys Arg Ile Ser Phe Leu Ile Ile Gly Leu Ala Trp Gly Ile Ser
                165                 170                 175

Ala Leu Leu Ala Ser Pro Leu Ala Ile Phe Arg Glu Tyr Ser Leu Ile
                180                 185                 190

Glu Ile Ile Pro Asp Phe Glu Ile Val Ala Cys Thr Glu Lys Trp Pro
            195                 200                 205

Gly Glu Glu Lys Ser Ile Tyr Gly Thr Val Tyr Ser Leu Ser Ser Leu
        210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Asn
                245                 250                 255

Asp His Tyr His Gln Arg Arg Gln Lys Thr Thr Lys Met Leu Val Cys
                260                 265                 270

Val Val Val Val Phe Ala Val Ser Trp Leu Pro Leu His Ala Phe Gln
            275                 280                 285

Leu Ala Val Asp Ile Asp Ser Gln Val Leu Asp Leu Lys Glu Tyr Lys
        290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
                325                 330                 335

Leu Ser Ala Phe Arg Cys Glu Gln Arg Leu Asp Ala Ile His Ser Glu
                340                 345                 350

Val Ser Val Thr Phe Lys Ala Lys Lys Asn Leu Glu Val Arg Lys Asn
            355                 360                 365

Ser Gly Pro Asn Asp Ser Phe Thr Glu Ala Thr Asn Val
        370                 375                 380
```